US012747285B2

(12) United States Patent
Nascimento et al.

(10) Patent No.: US 12,747,285 B2
(45) Date of Patent: Sep. 29, 2026

(54) ANTI-HUMAN IMMUNODEFICIENCY VIRUS-1 ANTIBODIES AND METHODS FOR USES THEREOF

(71) Applicant: GRIFOLS DIAGNOSTIC SOLUTIONS INC., San Diego, CA (US)

(72) Inventors: Elisabete Nascimento, Emeryville, CA (US); Jody Melton Witt, Emeryville, CA (US)

(73) Assignee: GRIFOLS DIAGNOSTIC SOLUTIONS INC., San Diego, CA (US)

( * ) Notice: Subject to any disclaimer, the term of this patent is extended or adjusted under 35 U.S.C. 154(b) by 751 days.

(21) Appl. No.: 18/015,317

(22) PCT Filed: Jul. 13, 2021

(86) PCT No.: PCT/IB2021/056284

§ 371 (c)(1),
(2) Date: Jan. 9, 2023

(87) PCT Pub. No.: WO2022/013730

PCT Pub. Date: Jan. 20, 2022

(65) Prior Publication Data

US 2024/0239876 A1 Jul. 18, 2024

Related U.S. Application Data

(60) Provisional application No. 63/051,323, filed on Jul. 13, 2020.

(51) Int. Cl.
*G01N 33/543* (2006.01)
*C07K 16/114* (2026.01)
*G01N 33/569* (2006.01)

(52) U.S. Cl.
CPC ........ *C07K 16/1143* (2026.01); *G01N 33/543* (2013.01); *G01N 33/56988* (2013.01); *C07K 2317/52* (2013.01); *C07K 2317/565* (2013.01); *G01N 2333/161* (2013.01)

(58) Field of Classification Search
None
See application file for complete search history.

(56) References Cited

U.S. PATENT DOCUMENTS

| | | | |
|---|---|---|---|
| 7,531,640 | B2 | 5/2009 | Lou et al. |
| 2010/0291076 | A1 | 11/2010 | Paralkar et al. |
| 2010/0311954 | A1 | 12/2010 | Chamberlain et al. |
| 2011/0195021 | A1 | 8/2011 | Deckert et al. |

FOREIGN PATENT DOCUMENTS

| | | | |
|---|---|---|---|
| CA | 2809363 | 3/2012 | |
| CA | 2831111 | 10/2012 | |
| CA | 2875703 | 12/2013 | |
| CA | 2896076 | 6/2014 | |
| CA | 2969940 | 6/2016 | |
| CN | 107223136 | 9/2017 | |
| EP | 0330359 A2 * | 8/1989 | ......... C07K 16/1054 |
| EP | 0345461 | 9/1994 | |
| EP | 3085386 | 9/2008 | |
| EP | 3219732 | 3/2010 | |
| EP | 2609114 | 4/2018 | |
| EP | 3309172 | 4/2018 | |
| WO | WO 2007/016240 | 2/2007 | |
| WO | WO 2007/020965 | 2/2007 | |
| WO | WO 2007/024222 | 3/2007 | |
| WO | WO 2009/052435 | 4/2009 | |
| WO | WO 2010/051470 | 5/2010 | |
| WO | WO 2010/104761 | 9/2010 | |
| WO | WO 2013/054127 | 4/2013 | |
| WO | WO 2018/014068 | 1/2018 | |
| WO | WO 2018/146230 | 8/2018 | |

OTHER PUBLICATIONS

Harlow et al. (Antibodies, A Laboratory Manual, Cold Spring Harbor laboratory, 1988, pp. 25-26 and 37-59) (Year: 1988).*

Edwards et al. ("The remarkable flexibility of the human antibody repertoire; isolation of over one thousand different antibodies to a single protein, BLyS" J. Mol. Biol. (2003) 334, 103-118, DOI: 10.1016/j.jmb.2003.09.054) (Year: 2003).*

Meyer et al. ("New Insights in Type I and II CD20 Antibody Mechanisms-of-Action With a Panel of Novel CD20 Antibodies", British Journal of Haematology, 2018, 180, 808-820, |https://doi.org/10.1111/bjh. 15132) (Year: 2018).*

Brown et al. ("Tolerance of single, but not multiple, amino acid replacements in antibody VH CDR 2: a means of minimizing B cell wastage from somatic hypermutation?", J Immunol. May 1996;156(9):3285-91) (Year: 1996).*

Vajdos et al. ("Comprehensive functional maps of the antigen-binding site of an anti-ErbB2 antibody obtained with shotgun scanning mutagenesis" J Mol Biol. Jul. 5, 2002;320(2):415-28, DOI: 10.1016/S0022-2836(02)00264-4) (Year: 2002).*

(Continued)

*Primary Examiner* — Ellen J Marcsisin

(74) *Attorney, Agent, or Firm* — Knobbe, Martens, Olson & Bear LLP

(57) ABSTRACT

An anti-HIV-1 antibody includes L-CDR1, L-CDR2 and L-CDR3. L-CDR1 is one of SEQ ID NO: 15, SEQ ID NO: 18, SEQ ID NO: 21, and a sequence that differs from SEQ ID NOs: 15, 18, or 21 by one or two substitutions, deletions, or additions. The amino acid sequence of L-CDR2 is one of SEQ ID NO: 16, SEQ ID NO: 19, SEQ ID NO: 22, and a sequence that differs from SEQ ID NOs: 16, 19, or 22 by one or two substitutions, deletions, or additions. The amino acid sequence of L-CDR3 is one of SEQ ID NO: 17, SEQ ID NO: 20, SEQ ID NO: 23, and a sequence that differs from SEQ ID NOs: 17, 20, or 23 by one or two substitutions, deletions, or additions.

20 Claims, 10 Drawing Sheets

Specification includes a Sequence Listing.

(56) References Cited

OTHER PUBLICATIONS

Alexander TS. Human Immunodeficiency Virus Diagnostic Testing: 30 Years of Evolution. Clinical and Vaccine Immunology 2016, vol. 23(4);249-53.

Codoner, F., et al. Gag protease coevolution analyses define novel structural surfaces in the HIV-1 matrix and capsid involved in resistance to Protease Inhibitors. Scientific Reports 2017, vol. 7(3717);1-10.

Chothia et al., Conformations of immunoglobulin hypervariable regions, Nature vol. 3 42:877-883, 1989.

Gray, E.R. et al. Unravelling the Molecular Basis of High Affinity Nanobodies against HIV p24: In Vitro Functional, Structural, and in Silico Insights, ACS Infectious Diseases, vol. 3, No. 7, Jul. 14, 2017 (Jul. 14, 2017), pp. 479-491.

Gray, E.R., et al., p24 revisited: a landscape review of antigen detection for early HIV diagnosis, AIDS 2018, 32:2089-2102.

Lefranc, et al., IMGT, the international ImMunoGeneTics information system, Nucleic Acids Research, 2005, vol. 33, D593-D597.

Lefranc, et al. IMGT® and 30 Years of Immunoinformatics Insight in Antibody V and C Domain Structure and Function, Antibodies 2019, 8; doi: 10.3390/antib8l20029.

Lewis J., et al. Field accuracy of fourth-generation rapid diagnostic tests for acute HIV-1: a systematic review. AIDS 2015, vol. 29(18);2465-71.

Liao-Chan S., et al., Monoclonal Antibody Binding-site Diversity Assessment with a Cell-based Clustering Assay. Journal of Immunological Methods 2014, vol. 405;1-14.

Maccallum et al., Antibody-antigen Interactions: Contact Analysis and Binding Site Topography. J. Mol. Biol., 262:732-745, 1996.

Retter et al., VBASE2, an integrative V gene database, Nucleic Acids Research, 33 (Database issue): D671-D674 (2005).

Soliman, M., et al. Mechanisms of HIV Control. Current HIV/AIDS Reports 2017, vol. 14(3);101-9.

Stone, M., et al. Comparison of detection limits of fourth- and fifth-generation combination HIV antigen-antibody, p24 antigen, and viral load assays on diverse HIV isolates. Journal of Clinical Microbiology 2018, vol. 56(8);1-12.

Makabe, et al. Thermodynamic Consequences of Mutations in Vernier Zone Residues of a Humanized Anti-human Epidermal Growth Factor Receptor Murine Antibody, 528* The Journal of Biological Chemistry vol. 283, No. 2, pp. 1156-1166, Jan. 11, 2008 DOI 10.1074/jbc.M706190200.

First Office Action for TW Application No. 110125750 issued on Aug. 13, 2024, which is related to the present application.

International Preliminary Report on Patentability issued Jan. 17, 2023; in PCT/IB2021/056284, which is related to the present application.

PCT Invitation to Pay Additional Search Fees issued Sep. 29, 2021; in PCT/IB2021/056284, which is related to the present application.

International Search Report & Written Opinion issued Sep. 20, 2021; in PCT/IB2021/056284, which is related to the present application.

* cited by examiner

| | Peak Label | RT (min) | % Area | Peak Size (kDa) | Name |
|---|---|---|---|---|---|
| 1 | 1 | 2.908 | 0.19 | -- - | Peak 1 |
| 2 | 2 | 3.361 | 0.46 | -- - | Peak 2 |
| 3 | 3 | 3.882 | 99.12 | -- - | Peak 3 |
| 4 | 4 | 4.844 | 0.23 | -- - | Peak 4 |

| | Peak Label | RT (min) | % Area | Peak Size (kDa) | Name |
|---|---|---|---|---|---|
| 1 | 1 | 3.982 | 0.24 | -- - | Peak 1 |
| 2 | 2 | 4.558 | 99.76 | -- - | Peak 2 |

| | Peak Label | RT (min) | % Area | Peak Size (kDa) | Name |
|---|---|---|---|---|---|
| 1 | 1 | 4.194 | 100.00 | -- - | Peak 1 |

ANTI-HUMAN IMMUNODEFICIENCY VIRUS-1 ANTIBODIES AND METHODS FOR USES THEREOF

REFERENCE TO SEQUENCE LISTING

The present application includes an Electronic Sequence Listing in ST.25 format. The Electronic Sequence Listing is updated as a file entitled HGF039001APCSEQLISTING.txt created on Apr. 13, 2026, which is approximately 49,027 bytes in size. The information in the Electronic Sequence Listing is incorporated herein by reference in its entirety.

TECHNICAL FIELD

This application relates to antibodies against Human Immunodeficiency Virus-1 (anti-HIV-1) that specifically bind to HIV-1 p24 protein. The present invention also refers to methods and assays for detection of HIV-1 in samples using said antibodies.

BACKGROUND

The human immunodeficiency virus 1 (HIV-1) is a retrovirus that infects 37.9 million people worldwide, killing around 1 million individuals every year, particularly in vulnerable populations unable to access diagnosis and treatment (Soliman, M., et al. *Mechanisms of HIV Control. Current HIV/AIDS Reports* 2017, vol. 14(3); 101-9). HIV-1 is the leading cause of acquired immune deficiency syndrome (AIDS), an incurable disease transmitted through sexual contact from HIV-1 infected individuals or by exposure to blood or blood-derived contaminated products. The virus targets the immune system by destroying and impairing the function of immune cells. Infected individuals become immunodeficient and susceptible to other opportunistic infections as well as some types of cancer (WHO website source—https://www.who.int/news-room/fact-sheets/detail/hiv-aids). Currently, only 46% of HIV-1 infected individuals know their infectious status. Hence, detection of HIV-1 in acute infection is a critical public health concern (Stone, M., et al. *Comparison of detection limits of fourth-and fifth-generation combination HIV antigen-antibody, p24 antigen, and viral load assays on diverse HIV isolates. Journal of Clinical Microbiology* 2018, vol. 56(8); 1-12).

In this particular context, the goal is to diagnose HIV-1 in the weeks immediately after an individual contracted the infection (acute phase) as this will likely prevent secondary transmission and allow for early access to treatment and care (Lewis J., et al. *Field accuracy of fourth-generation rapid diagnostic tests for acute HIV-1: a systematic review. AIDS* 2015, vol. 29(18); 2465-71). To achieve this goal in a timely manner, the use of early biomarkers for HIV-1 detection is key. Among the most commonly used biomarkers for diagnosis of HIV-1 infection are antibodies against the viral structural proteins. Here, p24 is considered an important biomarker for early HIV-1 detection, as it is the most abundant structural protein of the HIV-1 viral envelope and it is secreted at high levels in the blood serum during the initial stages of infection. p24 is a polymerized capsid protein that acts as the major structural component of the HIV-1 envelope around the viral RNA molecule. p24 is a 24-25 kDa protein derived from a Gag polyprotein precursor that, like the HIV-1 RNA, can be detected before seroconversion (Gray, E. R., et al. p24 revisited: *a landscape review of antigen detection for early HIV diagnosis. AIDS.* 2018, vol. 32(15); 2089-102).

Present guidelines from the Centers for Disease Control and Prevention (CDC) and the World Health Organization (WHO) recommend the use of fourth generation antibody-antigen assays as a preferred method for HIV-1 screening. These tests detect p24 antigen and anti-HIV-1 antibodies and have narrowed the diagnostic window period from 4 to 2 weeks post-exposure (Gray, E. R., et al. p24 revisited: *a landscape review of antigen detection for early HIV diagnosis. AIDS.* 2018, vol. 32(15); 2089-102; Codoner, F., et al. *Gag protease coevolution analyses define novel structural surfaces in the HIV-1 matrix and capsid involved in resistance to Protease Inhibitors. Scientific Reports* 2017, vol. 7(3717); 1-10; Alexander T S. *Human Immunodeficiency Virus Diagnostic Testing:* 30 Years of Evolution. *Clinical and Vaccine Immunology* 2016, vol. 23(4); 249-53; WHO. *World Health Organization Model List of Essential In Vitro Diagnostics.* 1st ed. Geneva. 2018; Centers for Disease Control and Prevention. 2017. National HIV testing day and new testing recommendations. Morbidity and Mortality Weekly Report vol. 63(25); 537-37).

However, there is still a need for anti HIV-1 antibodies that specifically bind to p24 antigen with high binding capacity and good manufacturing characteristics, since some antibodies currently commercially available show low sensitivity for early p24 detection.

Thus, the present invention provides anti-HIV-1 antibodies having improved binding capacity to HIV-1 p24 protein when compared to similar commercial reagents. These antibodies recognize novel, non-cross-reactive epitopes and can be used as single entities or as capture/detection partners in multiple HIV-1 immunoassays, such as immunodiagnostic or blood screening platforms.

SUMMARY

Where the present specification speaks to the sequence of CDR X or a sequence that differs from CDR X by one or two substitutions, deletions, or additions it is to be understood that such substitutions, deletions, or additions can arise at any amino acid of the range of amino acids defined by CDR X. The present specification individualizes each particular amino acid within the range of amino acids defined by CDR X as being suitable for such substitutions, deletions, or additions.

As a non-limiting illustration, L-CDR1 for Antibody #A can be defined as comprising the sequence of amino acids (1)-(11), RASQDISNYLH [as outlined in SEQ ID NO: 15]. Each of positions 1, 2, 3, 4, 5, 6, 7, 8, 9, 10, and 11 is to be considered suitable for a substitution, deletion, or addition unless otherwise specified or later refined by amendment.

In a first aspect, the present invention discloses an anti-HIV-1 antibody comprising a light chain comprising complementary determining regions L-CDR1, L-CDR2 and L-CDR3, wherein the amino acid sequence of L-CDR1 is selected from the group consisting of SEQ ID NO: 15, SEQ ID NO: 18, SEQ ID NO: 21, and a sequence that differs from anyone of SEQ ID NO: 15, 18, or 21 by one or two substitutions, deletions, or additions, the amino acid sequence of L-CDR2 is selected from the group consisting of SEQ ID NO: 16, SEQ ID NO: 19, SEQ ID NO: 22, and a sequence that differs from anyone of SEQ ID NO: 16, 19, or 22 by one or two substitutions, deletions, or additions, and the amino acid sequence of L-CDR3 is selected from the group consisting of SEQ ID NO: 17, SEQ ID NO: 20, SEQ ID NO: 23, and a sequence that differs from anyone of SEQ ID NO: 17, 20, or 23 by one or two substitutions, deletions, or additions.

In other embodiments, the anti-HIV-1 antibody of the present invention comprises a heavy chain comprising complementary determining regions H-CDR1, H-CDR2 and H-CDR3, wherein the amino acid sequence of H-CDR1 is selected from the group consisting of SEQ ID NO: 24, SEQ ID NO: 27, SEQ ID NO: 30, and a sequence that differs from anyone of SEQ ID NO: 24, 27, or 30 by one or two substitutions, deletions, or additions, the amino acid sequence of H-CDR2 is selected from the group consisting of SEQ ID NO: 25, SEQ ID NO: 28, SEQ ID NO: 31, and a sequence that differs from anyone of SEQ ID NO: 25, 28, or 31 by one or two substitutions, deletions, or additions, and the amino acid sequence of H-CDR3 is selected from the group consisting of SEQ ID NO: 26, SEQ ID NO: 29, SEQ ID NO: 32, and a sequence that differs from anyone of SEQ ID NO: 26, 29, or 32 by one or two substitutions, deletions, or additions.

In some embodiments, the light chain of the anti-HIV-1 antibody of the present invention comprises a sequence having about 90% homology with the amino acid sequence of SEQ ID NO: 7, or SEQ ID NO: 8, or SEQ ID NO: 9. In other embodiments, the light chain comprises the amino acid sequence of SEQ ID NO: 7, or SEQ ID NO: 8, or SEQ ID NO: 9.

In some embodiments, the heavy chain of the anti-HIV-1 antibody of the present invention comprises a sequence having about 90% homology with the amino acid sequence of SEQ ID NO: 10, SEQ ID NO: 11, or SEQ ID NO: 12. In other embodiments, the heavy chain comprises the amino acid sequence of SEQ ID NO: 10, SEQ ID NO: 11, or SEQ ID NO: 12.

In some embodiments, the amino acid sequence of L-CDR1 comprises SEQ ID NO: 15, or a sequence that differs from SEQ ID NO: 15 by one or two substitutions, deletions, or additions, the amino acid sequence of L-CDR2 comprises SEQ ID NO: 16, or a sequence that differs from SEQ ID NO: 16 by one or two substitutions, deletions, or additions, and the amino acid sequence of L-CDR3 comprises SEQ ID NO: 17, or a sequence that differs from SEQ ID NO: 17 by one or two substitutions, deletions, or additions. In other embodiments, the amino acid sequence of L-CDR1 comprises SEQ ID NO: 18, or a sequence that differs from SEQ ID NO: 18 by one or two substitutions, deletions, or additions, the amino acid sequence of L-CDR2 comprises SEQ ID NO: 19, or a sequence that differs from SEQ ID NO: 19 by one or two substitutions, deletions, or additions, and the amino acid sequence of L-CDR3 is SEQ ID NO: 20 or a sequence that differs from SEQ ID NO: 20 by one or two substitutions, deletions, or additions. In other embodiments, the amino acid sequence of L-CDR1 comprises SEQ ID NO: 21, or a sequence that differs from SEQ ID NO: 21 by one or two substitutions, deletions, or additions, the amino acid sequence of L-CDR2 comprises SEQ ID NO: 22, or a sequence that differs from SEQ ID NO: 22 by one or two substitutions, deletions, or additions, and the amino acid sequence of L-CDR3 comprises SEQ ID NO: 23 or a sequence that differs from SEQ ID NO: 23 by one or two substitutions, deletions, or additions.

In some embodiments, the amino acid sequence of H-CDR1 comprises SEQ ID NO: 24, or a sequence that differs from SEQ ID NO: 24 by one or two substitutions, deletions, or additions, the amino acid sequence of H-CDR2 comprises SEQ ID NO: 25, or a sequence that differs from SEQ ID NO: 25 by one or two substitutions, deletions, or additions, and the amino acid sequence of H-CDR3 comprises SEQ ID NO: 26, or a sequence that differs from SEQ ID NO: 26 by one or two substitutions, deletions, or additions. In other embodiments, the amino acid sequence of H-CDR1 comprises SEQ ID NO: 27, or a sequence that differs from SEQ ID NO: 27 by one or two substitutions, deletions, or additions, the amino acid sequence of H-CDR2 comprises SEQ ID NO: 28, or a sequence that differs from SEQ ID NO: 28 by one or two substitutions, deletions, or additions, and the amino acid sequence of H-CDR3 comprises SEQ ID NO: 29 or a sequence that differs from SEQ ID NO: 29 by one or two substitutions, deletions, or additions. In other embodiments, the amino acid sequence of H-CDR1 comprises SEQ ID NO: 30, or a sequence that differs from SEQ ID NO: 30 by one or two substitutions, deletions, or additions, the amino acid sequence of H-CDR2 comprises SEQ ID NO: 31, or a sequence that differs from SEQ ID NO: 31 by one or two substitutions, deletions, or additions, and the amino acid sequence of H-CDR3 comprises SEQ ID NO: 32 or a sequence that differs from SEQ ID NO: 32 by one or two substitutions, deletions, or additions.

In some embodiments, the amino acid sequence of L-CDR1 comprises SEQ ID NO: 15 or a sequence that differs from SEQ ID NO: 15 by one or two substitutions, deletions, or additions, the amino acid sequence of L-CDR2 comprises SEQ ID NO: 16 or a sequence that differs from SEQ ID NO: 16 by one or two substitutions, deletions, or additions, the amino acid sequence of L-CDR3 comprises SEQ ID NO: 17 or a sequence that differs from SEQ ID NO: 17 by one or two substitutions, deletions, or additions, the amino acid sequence of H-CDR1 comprises SEQ ID NO: 24 or a sequence that differs from SEQ ID NO: 24 by one or two substitutions, deletions, or additions, the amino acid sequence of H-CDR2 comprises SEQ ID NO: 25 or a sequence that differs from SEQ ID NO: 25 by one or two substitutions, deletions, or additions, and the amino acid sequence of H-CDR3 comprises SEQ ID NO: 26 or a sequence that differs from SEQ ID NO: 26 by one or two substitutions, deletions, or additions.

In some embodiments, the amino acid sequence of L-CDR1 comprises SEQ ID NO: 18 or a sequence that differs from SEQ ID NO: 18 by one or two substitutions, deletions, or additions, the amino acid sequence of L-CDR2 comprises SEQ ID NO: 19 or a sequence that differs from SEQ ID NO: 19 by one or two substitutions, deletions, or additions, the amino acid sequence of L-CDR3 comprises SEQ ID NO: 20 or a sequence that differs from SEQ ID NO: 20 by one or two substitutions, deletions, or additions, the amino acid sequence of H-CDR1 comprises SEQ ID NO: 27 or a sequence that differs from SEQ ID NO: 27 by one or two substitutions, deletions, or additions, the amino acid sequence of H-CDR2 comprises SEQ ID NO: 28 or a sequence that differs from SEQ ID NO: 28 by one or two substitutions, deletions, or additions, and the amino acid sequence of H-CDR3 comprises SEQ ID NO: 29 or a sequence that differs from SEQ ID NO: 29 by one or two substitutions, deletions, or additions.

In some embodiments, the amino acid sequence of L-CDR1 comprises SEQ ID NO: 21 or a sequence that differs from SEQ ID NO: 21 by one or two substitutions, deletions, or additions, the amino acid sequence of L-CDR2 comprises SEQ ID NO: 22 or a sequence that differs from SEQ ID NO: 22 by one or two substitutions, deletions, or additions, the amino acid sequence of L-CDR3 comprises SEQ ID NO: 23. or a sequence that differs from SEQ ID NO: 23 by one or two substitutions, deletions, or additions, the amino acid sequence of H-CDR1 comprises SEQ ID NO: 30 or a sequence that differs from SEQ ID NO: 30 by one or two substitutions, deletions, or additions, the amino acid sequence of H-CDR2 comprises SEQ ID NO: 31 or a sequence that differs from SEQ ID NO: 31 by one or two substitutions, deletions, or additions, and the amino acid sequence of H-CDR3 comprises SEQ ID NO: 32 or a sequence that differs from SEQ ID NO: 32 by one or two substitutions, deletions, or additions.

In some embodiments, the light chain of the anti-HIV-1 antibody of the present invention comprises the amino acid sequence selected from the group consisting of SEQ ID NO: 1, SEQ ID NO: 2, or SEQ ID NO: 3.

In some embodiments, the heavy chain of the anti-HIV-1 antibody of the present invention comprises the amino acid sequence selected from the group consisting of SEQ ID NO: 4, SEQ ID NO: 5, or SEQ ID NO: 6.

In some embodiments, the anti-HIV-1 antibody of the present invention specifically binds to an epitope of HIV-1 p24 protein comprising the amino acid sequence of SEQ ID NO: 33.

In some embodiments, the amino acid sequence of L-CDR1 of the anti-HIV-1 antibody of the present invention comprises SEQ ID NO: 21 or a sequence that differs from SEQ ID NO: 21 by one or two substitutions, deletions, or additions, the amino acid sequence of L-CDR2 comprises SEQ ID NO: 22 or a sequence that differs from SEQ ID NO: 22 by one or two substitutions, deletions, or additions, and the amino acid sequence of L-CDR3 comprises SEQ ID NO: 23. or a sequence that differs from SEQ ID NO: 23 by one or two substitutions, deletions, or additions.

In some embodiments, the amino acid sequence of H-CDR1 of the anti-HIV-1 antibody of the present invention comprises SEQ ID NO: 30 or a sequence that differs from SEQ ID NO: 30 by one or two substitutions, deletions, or additions, the amino acid sequence of H-CDR2 comprises SEQ ID NO: 31 or a sequence that differs from SEQ ID NO: 31 by one or two substitutions, deletions, or additions, and the amino acid sequence of H-CDR3 comprises SEQ ID NO: 32 or a sequence that differs from SEQ ID NO: 32 by one or two substitutions, deletions, or additions.

In some preferred embodiments, the light chain of said antibody comprises the amino acid sequence selected from the group consisting of SEQ ID NO: 1, SEQ ID NO: 2, or SEQ ID NO: 3 and the heavy chain of said antibody comprises the amino acid sequence selected from the group consisting of SEQ ID NO: 4, SEQ ID NO: 5, or SEQ ID NO: 6.

In some embodiments, the anti-HIV-1 antibody of the present invention is a monoclonal antibody or a recombinant antibody. In other embodiments, said antibody is an antibody fragment. When the anti-HIV-1 antibody is an antibody fragment, it is selected from variable fragments (Fv), single-chain Fvs (scFv), bispecific antibodies (sc(Fv)2), single chain antibodies, single domain antibodies, Fab fragments, F(ab')2 fragments, Fab' fragments, disulfide-linked Fv (dsFv), chemically conjugated Fv (ccFv), diabodies, anti-idiotypic (anti-Id) antibodies, affibodies, nanobodies, and unibodies.

In some embodiments, the anti-HIV-1 antibody comprises a constant region of the murine IgG1 class or the murine IgG2a class.

In some embodiments the anti-HIV-1 antibody is bound to a solid support.

In some aspects, the present invention discloses a cell comprising the anti-HIV-1 antibody of the present invention.

In other aspects, the present invention discloses a nucleic acid comprising a nucleotide sequence encoding the anti-HIV-1 antibody, a promoter operably linked to the nucleotide sequence and a selectable marker. A cell comprising said nucleic acid is also disclosed herein.

The present invention also discloses compositions comprising the anti-HIV-1 antibody as described herein, and a solid support, wherein the anti-HIV-1 antibody is covalently or non-covalently bound to the solid support. In some embodiments, the solid support comprises a particle, a bead, a membrane, a surface, a polypeptide chip, a microtiter plate, or the solid-phase of a chromatography column.

The present invention also discloses kits for detecting the presence of HIV-1 in a sample, said kit comprising at least one anti-HIV-1 antibody according to the present invention and a solid support, wherein said at least one antibody is covalently or non-covalently bound to a solid support.

DETAILED DESCRIPTION

Figure 1:
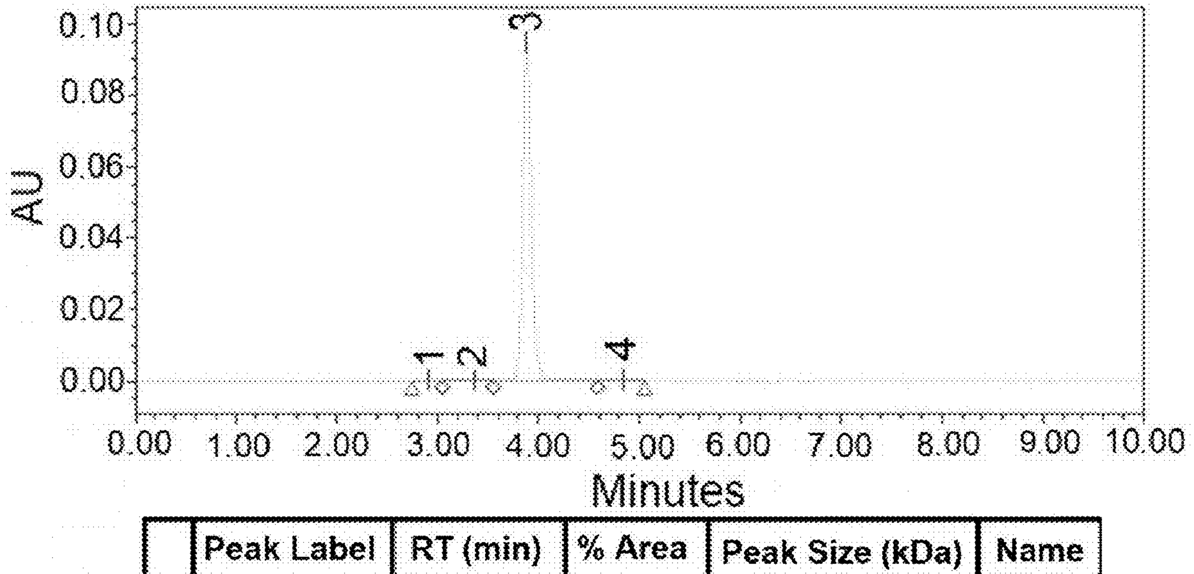
FIG. 1. SE-UPLC analysis % monomer for antibody #A and SDS-PAGE for antibody #A single clones (lanes 1, 2 and 3 represent subclones ran in reducing and non-reducing conditions, respectively).
Figure 1:
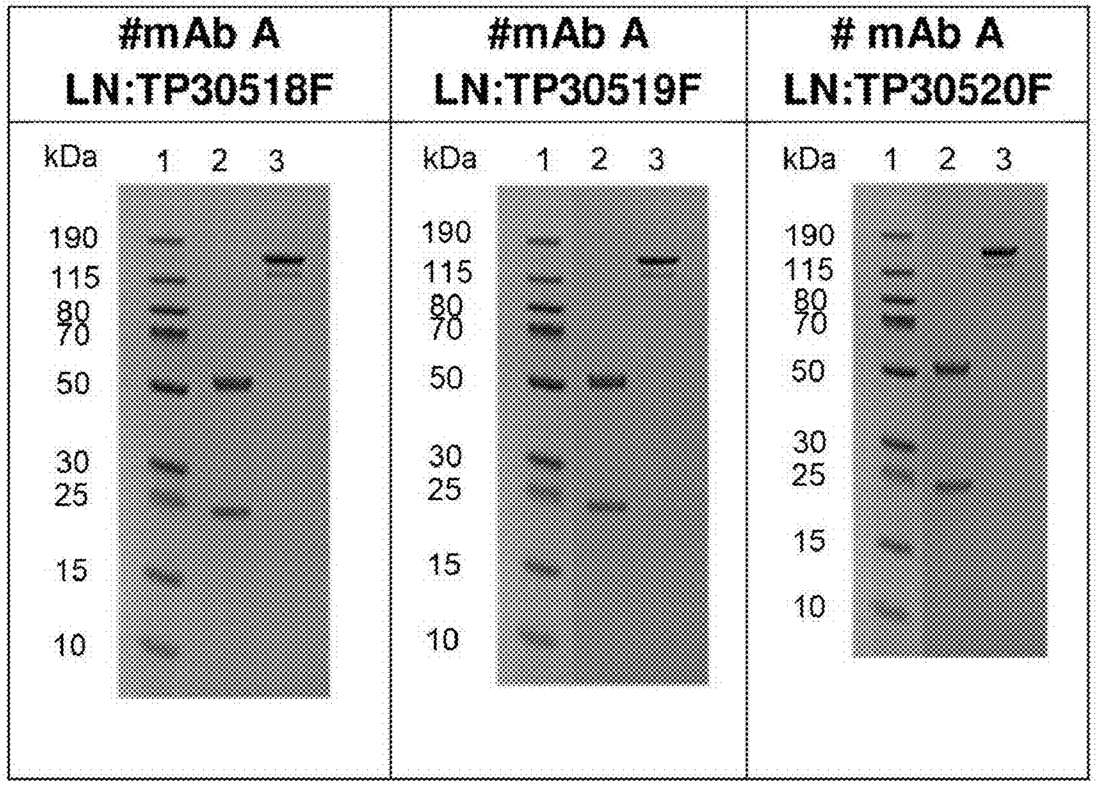

The following description is merely intended to illustrate various embodiments of the present disclosure. As such, the specific modifications discussed are not intended to be limiting. It will be apparent to one skilled in the art that various equivalents, changes, and modifications may be made without departing from the spirit or scope of the subject matters presented herein, and it is understood that such equivalent embodiments are to be included herein.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used and will be apparent to those of skill in the art. All publications and other references mentioned herein are incorporated by reference in their entirety. In case of conflict, the present specification, including definitions, will control. The materials, methods, and examples are illustrative only and not intended to be limiting.

Each embodiment in this specification is to be applied mutatis mutandis to every other embodiment unless expressly stated otherwise.

The following terms, unless otherwise indicated, shall be understood to have the following meanings:

As used herein, the term "nucleic acid" refers to any materials comprised of DNA or RNA. Nucleic acids can be made synthetically or by living cells.

A "nucleotide," as used herein, is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits.

As used herein, the term "polynucleotide" refers to a polymeric chain of nucleotides. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native inter-nucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

As used herein, the term "protein" or refers to large biological molecules, or macromolecules, consisting of one or more chains of amino acid residues. Many proteins are enzymes that catalyze biochemical reactions and are vital to metabolism. Proteins also have structural or mechanical functions, such as actin and myosin in muscle and the proteins in the cytoskeleton, which form a system of scaffolding that maintains cell shape. Other proteins are important in cell signalling, immune responses, cell adhesion, and the cell cycle. However, proteins may be completely artificial or recombinant, i.e., not existing naturally in a biological system.

As used herein, the term "polypeptide" refers to both naturally-occurring and non-naturally-occurring proteins, and fragments, mutants, derivatives and analogs thereof. A polypeptide may be monomeric or polymeric. A polypeptide may comprise a number of different domains (peptides) each of which has one or more distinct activities.

As used herein, the term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, the term "fusion protein" refers to proteins comprising two or more amino acid sequences that do not co-exist in naturally-occurring proteins. A fusion protein may comprise two or more amino acid sequences from the same or from different organisms. The two or more amino acid sequences of a fusion protein are typically in frame without stop codons between them and are typically translated from mRNA as part of the fusion protein.

The term "fusion protein" and the term "recombinant" when referring to a protein according to (3), can be used interchangeably herein.

The terms "antibody" or "immunoglobulin", as used herein, have the same meaning, and are used equally in the present invention. The term "antibody" as used herein refers to immunoglobulin molecules and immunologically active portions of immunoglobulin molecules, i.e., molecules that contain an antigen binding site that specifically binds an antigen. As such, the term antibody encompasses not only whole antibody molecules, but also antibody fragments or derivatives.

In natural antibodies, two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, normally includes six CDRs, comprising the CDR set from each of a heavy and a light chain V region. Framework Regions (FRs) refer to amino acid sequences interposed between CDRs.

CDR can be identified in accordance with the definitions of the Kabat, Chothia, the accumulation of both Kabat and Chothia, AbM, contact, IMGT unique numbering, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others (See, e.g., Chothia et al., Nature 342:877-883, 1989). Other approaches to CDR identification include the "AbM definition," which is a compromise between Kabat and Chothia and is derived using Oxford Molecular's AbM antibody modeling software (now Accelrys0), the "contact definition" of CDRs based on observed antigen contacts, set forth in MacCallum et al., J. Mol. Biol., 262:732-745, 1996, or "IMGT unique numbering", which relies on the high conservation of the structure of the variable region (see Lefranc, M.-P. Nucl. Acids Res., 33, D593-D597, 2005). In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, IMGT unique numbering and/or conformational definitions, unless otherwise specified.

Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. Unless otherwise indicated, all CDRs set forth herein are derived according to the Abysis database website as per the scheme indicated.

As used herein, the terms "antibody" include isolated antibodies, polyclonal antibodies, monoclonal antibodies, multispecific antibodies, human antibodies, humanized antibodies (fully or partially humanized), animal antibodies, recombinant antibodies, chimeric antibodies, and antibody fragments.

As used herein, the term "monoclonal antibody" or "mAb" refers to an antibody composition having a homogeneous antibody population that bind to the same epitope. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas. The term also encompasses antibodies obtained by other methods for production of monoclonal antibodies known in the art, such as the establishment of eukaryotic cells lines by transient or stable transfection.

As used herein, the term "recombinant antibody" refers to an antibody that is expressed from a cell or cell line transfected with one or more expression vectors comprising the coding sequence of the antibody, where said coding sequence is not naturally associated with the cell. Recombinant antibodies or fragments thereof are prepared, expressed, created or isolated by any recombinant mean, as well known by the skilled person.

In some embodiments, a "recombinant antibody" may also be a "monoclonal antibody" when it derives from a homogeneous antibody population that binds to the same epitope.

Thus, the term "antibody fragments" as used herein, include but are not limited to variable fragments (Fv), single-chain Fvs (scFv), bispecific antibodies ($sc(Fv)_2$), single chain antibodies, single domain antibodies, Fab fragments, $F(ab')_2$ fragments, Fab' fragments, disulfide-linked Fv (dsFv), chemically conjugated Fv (ccFv), diabodies and anti-idiotypic (anti-Id) antibodies, and functionally active epitope-binding fragments of any of the above. In certain embodiments antibodies also include affibodies, nanobodies, and unibodies. In certain embodiments particular antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG1, IgG2, IgG3, IgG4, IgAi and IgA2) or subclass.

As used herein, the terms "antigen-binding fragment (Fab)" refers to antibodies fragments comprising one constant and one variable domain of each of the heavy and the light chain. The variable domain contains the antigen-binding sites. Generally, an antibody comprises a fragment crystallizable region (Fc) and two antigen-binding fragments (Fab). The Fab fragments can be separated from the Fc region resulting in two Fab fragments, which is also known as $F(ab')_2$ fragment or dimeric fragment antigen binding.

The term "isolated" refers to a protein (e.g., an antibody) or nucleic acid that is substantially free of other cellular material and/or chemicals. For example, when an isolated antibody is expressed by a cell from a different species, e.g., a human antibody expressed in a murine cell, and is substantially free of other proteins from the different species. A protein may be rendered substantially free of naturally associated components (or components associated with the cellular expression system used to produce the antibody) by isolation, using protein purification techniques well known in the art.

As used herein, the term "antigen" refers to a biomolecule that binds specifically to the respective antibody. An antibody from the diverse repertoire binds a specific antigenic structure by means of its variable region interaction.

As used herein, the term "epitope" refers to the portion of an antigen to which an antibody specifically binds. Thus, the term "epitope" includes any protein determinant capable of specific binding to an immunoglobulin or T-cell receptor.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art.

The term "sample", as used herein, refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells.

The sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

The terms "patient" or "individual" are used interchangeably herein, and refers to a mammalian subject to be diagnosed or treated, with human patients being preferred. In some cases, the methods of the invention find use in experimental animals, in veterinary application, and in the development of animal models for disease, including, but not limited to, rodents including mice, rats, and hamsters; and primates.

The term "vector" refers to a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors).

Other vectors (e.g., non-episomal mammalian vectors) are integrated into the genome of a host cell upon introduction into the host cell, and thereby are replicated along with the host genome.

An "expression vector" is a type of vector that can direct the expression of a chosen polynucleotide. An "expression cell" is a cell that contains an expression vector.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements.

The term "diagnostic" or "diagnosed", as used herein, means identifying the presence or nature of a pathologic condition or a patient susceptible to a disease. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The term "binding affinity", as used herein, refers to the strength of interaction between an antigen's epitope and an antibody's antigen binding site.

The present invention relates to novel antibodies specific for the detection of Human Immunodeficiency Virus 1 (HIV-1) p24 protein. These antibodies recognize novel and non-cross-reactive epitopes of HIV-1 p24 protein and exhibit a higher degree of affinity and sensitivity when compared to other commercially-available products. Thus, the antibodies described herein can be utilized as diagnostic reagents, standards or positive controls in immunoassays for early HIV-1 detection. They can be used for detection of any of the three main HIV-1 groups (group M (main), group N (new), and group O (outlier)).

The present invention also relates to compositions and kits comprising said anti-HIV-1 antibodies for detecting the presence of HIV-1 in a sample.

I. Anti-HIV-1 Antibodies

As used herein, the terms "homology", "similarity" or "identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent homology/identity, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=#of identical positions/total #of positions (e.g., overlapping positions)×100). In some embodiments, the two sequences that are compared are the same length after gaps are introduced within the sequences, as appropriate (e.g., excluding additional sequence extending beyond the sequences being compared). For sequence comparisons between two sequences, a "corresponding" CDR refers to a CDR in the same location in both sequences (e.g., CDR-H1 of each sequence).

The determination of percent identity, percent similarity, or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. When utilizing BLAST and Gapped BLAST the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

In one embodiment described herein, the recombinant antibody comprises a light chain and a heavy chain. In other embodiment described herein, the recombinant antibody comprises two light chains and two heavy chains. The light chain(s) of the recombinant antibody of the present invention can comprise two domains, a variable domain (VL) and a constant domain (CL). The heavy chain(s) of the recombinant antibody of the present invention can comprise four domains, a variable domain (VH) and three constant domains (CH1, CH2 and CH3, collectively referred to as CH).

In some embodiments, the anti-HIV-1 antibody of the present invention is a monoclonal antibody.

In other embodiments, the anti-HIV-1 antibody of the present invention is a recombinant antibody.

In other embodiments, the anti-HIV-1 antibody is a recombinant monoclonal antibody according to the definitions of the present invention. In other embodiments, the anti-HIV-1 antibody is an isolated antibody.

In some embodiments, the anti-HIV-1 antibody is an antibody fragment. In a preferred embodiment, said antibody fragment is selected from variable fragments (Fv), single-chain Fvs (scFv), bispecific antibodies ($sc(Fv)_2$), single chain antibodies, single domain antibodies, Fab fragments, $F(ab')_2$ fragments, Fab' fragments, disulfide-linked Fv (dsFv), chemically conjugated Fv (ccFv), diabodies, anti-idiotypic (anti-Id) antibodies, affibodies, nanobodies, and unibodies.

In one embodiment described herein, the anti-HIV-1 antibody comprises the Fc region and the two Fab fragments. In other embodiment described herein, the anti-HIV-1 antibody is a fragment antigen binding and does not comprises the Fc region. In other embodiment described herein, the anti-HIV-1 antibody consists of one Fab fragment. In other embodiment described herein, the anti-HIV-1 antibody consists of two Fab fragments ($F(ab)_2$).

In one embodiment described herein, the anti-HIV-1 antibody may be of any type known by the skilled person (for example, IgG, IgE, IgM, IgD, IgA and IgY), or any class known by the skilled person (for example, IgG1, IgG2, IgG3, IgG4, IgAi and IgA2) or any known subclass.

In one embodiment described herein, the anti-HIV antibody is of the IgG type. In a preferred embodiment, the anti-HIV-antibody is of the IgG1, IgG2, IgG3 or IgG4 class. In another preferred embodiment, the anti-HIV-antibody is of the IgG1 or IgG2 class. In another preferred embodiment, the anti-HIV-antibody is of the IgG2a class.

The species of the constant region of the antibody of the present invention may be human, mouse, rabbit, rat, hamster, guinea pig, goat, sheep, horse, chicken, or a chimera of any of the foregoing species, although the species of the antibody of the present invention is not particularly limiting. In some preferred embodiments, the anti-HIV antibody of the present invention comprises a constant region of the murine IgG1 class or the murine IgG2a class.

A. Light Chain

In some embodiments described herein, the anti-HIV-1 antibody comprises a light chain comprising complementary determining regions (CDR). Said CDRs correspond to the sequences identified according to any CDR definition approach known by the skilled person. In some preferred embodiments, the CDRs regions correspond to the sequences identified according to Kabat numbering scheme. In other preferred embodiments, the CDRs regions may correspond to the sequences identified according to other numbering methods or a combination of Kabat and other numbering methods. For example, the CDR regions may correspond to the sequences identified according to the Chothia numbering scheme.

In some embodiments described herein, the anti-HIV-1 antibody comprises a light chain comprising complementary determining regions L-CDR1, L-CDR2 and L-CDR3, each of them comprising a sequence of at least five contiguous amino acids selected from the amino acid sequence of SEQ ID NO:7, or SEQ ID NO: 8, or SEQ ID NO: 9. In some preferred embodiments, the sequence of L-CDR1 is selected from the group consisting of SEQ ID NO: 15, SEQ ID NO: 18 and SEQ ID NO: 21. In some preferred embodiments, the sequence of L-CDR2 is selected from the group consisting of SEQ ID NO: 16, SEQ ID NO: 19 and SEQ ID NO: 22. In some preferred embodiments, the sequence of L-CDR3 is selected from the group consisting of SEQ ID NO: 17, SEQ ID NO: 20 and SEQ ID NO: 23. In other preferred embodiments, the sequence of L-CDR1 is selected from the group consisting of SEQ ID NO: 15, SEQ ID NO: 18 and SEQ ID NO: 21, the sequence of L-CDR2 is selected from the group consisting of SEQ ID NO: 16, SEQ ID NO: 19 and SEQ ID NO: 22, and the sequence of L-CDR3 is selected from the group consisting of SEQ ID NO: 17, SEQ ID NO: 20 and SEQ ID NO: 23.

In another embodiment described herein, the variable region of the light chain of the anti-HIV-1 antibody of the present invention comprises the amino acid sequence of SEQ ID NO: 7, or SEQ ID NO: 8, or SEQ ID NO: 9. In yet another embodiment, the variable region of the light chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 7, or SEQ ID NO: 8, or SEQ ID NO: 9. In some preferred embodiments, the light chain of the anti-HIV-1 antibody of the present invention comprises a sequence having about 90% homology with the amino acid sequence of SEQ ID NO: 7, or SEQ ID NO: 8, or SEQ ID NO: 9.

In another embodiment described herein, the recombinant antibody comprises a light chain comprising the amino acid sequence of SEQ ID NO: 1, SEQ ID NO: 2, or SEQ ID NO: 3. In other embodiment, the light chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 1, SEQ ID NO: 2, or SEQ ID NO: 3. In some preferred embodiments, the light chain of the anti-HIV-1 antibody of the present invention comprises a sequence having about 90% homology with the amino acid sequence of SEQ ID NO: 1, SEQ ID NO: 2, or SEQ ID NO: 3.

B. Heavy Chain

In some embodiments described herein, the anti-HIV-1 antibody comprises a heavy chain comprising complementary determining regions (CDR). Said CDRs correspond to the sequences identified according to any CDR definition approach known by the skilled person. In some preferred embodiments, the CDRs regions correspond to the sequences identified according to Kabat numbering scheme. In other preferred embodiments, the CDRs regions may correspond to the sequences identified according to other numbering methods or a combination of Kabat and other numbering methods. For example, the CDR regions may correspond to the sequences identified according to the Chothia numbering scheme.

In some embodiments described herein, the anti-HIV-1 antibody comprises a heavy chain comprising complementary determining regions H-CDR1, H-CDR2 and H-CDR3, each of them comprising a sequence of at least five contiguous amino acids selected from the amino acid sequence of SEQ ID NO: 10, or SEQ ID NO: 11, or SEQ ID NO: 12. In some preferred embodiments, the sequence of H-CDR1 is selected from the group consisting of SEQ ID NO: 24, SEQ ID NO: 27 and SEQ ID NO: 30. In some preferred embodiments, the sequence of H-CDR2 is selected from the group consisting of SEQ ID NO: 25, SEQ ID NO: 28 and SEQ ID NO: 31. In some preferred embodiments, the sequence of H-CDR3 is selected from the group consisting of SEQ ID NO: 26, SEQ ID NO: 29 and SEQ ID NO: 32. In some preferred embodiments, the sequence of H-CDR1 is selected from the group consisting of SEQ ID NO: 24, SEQ ID NO: 27 and SEQ ID NO: 30, the sequence of H-CDR2 is selected from the group consisting of SEQ ID NO: 25, SEQ ID NO: 28 and SEQ ID NO: 31, the sequence of H-CDR3 is selected from the group consisting of SEQ ID NO: 26, SEQ ID NO: 29 and SEQ ID NO: 32.

In another embodiment described herein, the variable region of the heavy chain of the anti-HIV-1 antibody of the present invention comprises the amino acid sequence of SEQ ID NO: 10, or SEQ ID NO: 11, or SEQ ID NO: 12. In yet another embodiment, the variable region of the heavy chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 10, or SEQ ID NO: 11, or SEQ ID NO: 12. In some preferred embodiments, the heavy chain of the anti-HIV-1 antibody of the present invention comprises a sequence having about 90% homology with the amino acid sequence of SEQ ID NO: 10, or SEQ ID NO: 11, or SEQ ID NO: 12.

In another embodiment described herein, the recombinant antibody comprises a heavy chain comprising the amino acid sequence of SEQ ID NO: 4, SEQ ID NO: 5, or SEQ ID NO: 6. In other embodiment, the light chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 4, SEQ ID NO: 5, or SEQ ID NO: 6. In some preferred embodiments, the heavy chain of the anti-HIV-1 antibody of the present invention comprises a sequence having about 90% homology with the amino acid sequence of SEQ ID NO: 4, SEQ ID NO: 5, or SEQ ID NO: 6.

C. Exemplary Anti-HIV-1 Antibodies

In one embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 15, the amino acid sequence of L-CDR2 is SEQ ID NO: 16, and the amino acid sequence of L-CDR3 is SEQ ID NO: 17.

In other embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 18, the amino acid sequence of L-CDR2 is SEQ ID NO: 19, and the amino acid sequence of L-CDR3 is SEQ ID NO: 20.

In other embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 21, the amino acid sequence of L-CDR2 is SEQ ID NO: 22, and the amino acid sequence of L-CDR3 is SEQ ID NO: 23.

In one embodiment described herein, the anti-HIV-1 antibody comprises a heavy chain comprising complementary determining regions H-CDR1, H-CDR2 and H-CDR3, wherein the amino acid sequence of H-CDR1 is SEQ ID NO: 24, the amino acid sequence of H-CDR2 is SEQ ID NO: 25, and the amino acid sequence of H-CDR3 is SEQ ID NO: 26.

In other embodiment described herein, the anti-HIV-1 antibody comprises a heavy chain comprising complementary determining regions H-CDR1, H-CDR2 and H-CDR3, wherein the amino acid sequence of H-CDR1 is SEQ ID NO: 27, the amino acid sequence of H-CDR2 is SEQ ID NO: 28, and the amino acid sequence of H-CDR3 is SEQ ID NO: 29.

In other embodiment described herein, the anti-HIV-1 antibody comprises a heavy chain comprising complementary determining regions H-CDR1, H-CDR2 and H-CDR3, wherein the amino acid sequence of H-CDR1 is SEQ ID NO: 30, the amino acid sequence of H-CDR2 is SEQ ID NO: 31, and the amino acid sequence of H-CDR3 is SEQ ID NO: 32.

The anti-HIV-1 antibodies of the present invention may comprise any combination of the CDR regions of both the light and heavy chains as described herein.

In a preferred embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 15, the amino acid sequence of L-CDR2 is SEQ ID NO: 16, and the amino acid sequence of L-CDR3 is SEQ ID NO: 17, and a heavy chain comprising complementary determining regions H-CDR1, H-CDR2 and H-CDR3, wherein the amino acid sequence of H-CDR1 is SEQ ID NO: 24, the amino acid sequence of H-CDR2 is SEQ ID NO: 25, and the amino acid sequence of H-CDR3 is SEQ ID NO: 26.

In a preferred embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 15, the amino acid sequence of L-CDR2 is SEQ ID NO: 16, and the amino acid sequence of L-CDR3 is SEQ ID NO: 17, and a heavy chain comprising complementary determining regions H-CDR1, H-CDR2 and H-CDR3, wherein the amino acid sequence of H-CDR1 is SEQ ID NO: 27, the amino acid sequence of H-CDR2 is SEQ ID NO: 28, and the amino acid sequence of H-CDR3 is SEQ ID NO: 29.

In a preferred embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 15, the amino acid sequence of L-CDR2 is SEQ ID NO: 16, and the amino acid sequence of L-CDR3 is SEQ ID NO: 17, and a heavy chain comprising complementary determining regions H-CDR1, H-CDR2 and H-CDR3, wherein the amino acid sequence of H-CDR1 is SEQ ID NO: 30, the amino acid sequence of H-CDR2 is SEQ ID NO: 31, and the amino acid sequence of H-CDR3 is SEQ ID NO: 32.

In a preferred embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 18, the amino acid sequence of L-CDR2 is SEQ ID NO: 19, and the amino acid sequence of L-CDR3 is SEQ ID NO: 20, and a heavy chain comprising complementary determining regions H-CDR1, H-CDR2 and H-CDR3, wherein the amino acid sequence of H-CDR1 is SEQ ID NO: 24, the amino acid sequence of H-CDR2 is SEQ ID NO: 25, and the amino acid sequence of H-CDR3 is SEQ ID NO: 26.

In a preferred embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 18, the amino acid sequence of L-CDR2 is SEQ ID NO: 19, and the amino acid sequence of L-CDR3 is SEQ ID NO: 20, and a heavy chain comprising complementary determining regions H-CDR1, H-CDR2 and H-CDR3, wherein the amino acid sequence of H-CDR1 is SEQ ID NO: 27, the amino acid sequence of H-CDR2 is SEQ ID NO: 28, and the amino acid sequence of H-CDR3 is SEQ ID NO: 29.

In a preferred embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 18, the amino acid sequence of L-CDR2 is SEQ ID NO: 19, and the amino acid sequence of L-CDR3 is SEQ ID NO: 20, and a heavy chain comprising complementary determining regions H-CDR1, H-CDR2 and H-CDR3, wherein the amino acid sequence of H-CDR1 is SEQ ID NO: 30, the amino acid sequence of H-CDR2 is SEQ ID NO: 31, and the amino acid sequence of H-CDR3 is SEQ ID NO: 32.

In a preferred embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 21, the amino acid sequence of L-CDR2 is SEQ ID NO: 22, and the amino acid sequence of L-CDR3 is SEQ ID NO: 23, and a heavy chain comprising complementary determining regions H-CDR1, H-CDR2 and H-CDR3, wherein the amino acid sequence of H-CDR1 is SEQ ID NO: 24, the amino acid sequence of H-CDR2 is SEQ ID NO: 25, and the amino acid sequence of H-CDR3 is SEQ ID NO: 26.

In a preferred embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 21, the amino acid sequence of L-CDR2 is SEQ ID NO: 22, and the amino acid sequence of L-CDR3 is SEQ ID NO: 23, and a heavy chain comprising complementary determining regions H-CDR1, H-CDR2 and H-CDR3, wherein the amino acid sequence of H-CDR1 is SEQ ID NO: 27, the amino acid sequence of H-CDR2 is SEQ ID NO: 28, and the amino acid sequence of H-CDR3 is SEQ ID NO: 29.

In a preferred embodiment described herein, the anti-HIV-1 antibody comprises a light chain comprising complementary determining regions L-CDR1, L-CDR2 and L-CDR3, wherein the amino acid sequence of L-CDR1 is SEQ ID NO: 21, the amino acid sequence of L-CDR2 is SEQ ID NO: 22, and the amino acid sequence of L-CDR3 is SEQ ID NO: 23, and a heavy chain comprising complementary determining regions H-CDR1, H-CDR2 and H-CDR3, wherein the amino acid sequence of H-CDR1 is SEQ ID NO: 30, the amino acid sequence of H-CDR2 is SEQ ID NO: 31, and the amino acid sequence of H-CDR3 is SEQ ID NO: 32.

In one embodiment described herein, the anti-HIV-1 antibody comprises a light chain comprising the amino acid sequence selected from the group consisting of SEQ ID NO: 7, SEQ ID NO: 8, or SEQ ID NO: 9 and a heavy chain comprising the amino acid sequence selected from the group consisting of SEQ ID NO: 10, SEQ ID NO: 11, or SEQ ID NO: 12.

In a preferred embodiment, the anti-HIV-1 antibody comprises a light chain comprising the amino acid sequence of SEQ ID NO: 7, and a heavy chain comprising the amino acid sequence of SEQ ID NO: 10.

In a preferred embodiment, the anti-HIV-1 antibody comprises a light chain comprising the amino acid sequence of SEQ ID NO: 7, and a heavy chain comprising the amino acid sequence of SEQ ID NO: 11.

In a preferred embodiment, the anti-HIV-1 antibody comprises a light chain comprising the amino acid sequence of SEQ ID NO: 7, and a heavy chain comprising the amino acid sequence of SEQ ID NO: 12.

In a preferred embodiment, the anti-HIV-1 antibody comprises a light chain comprising the amino acid sequence of SEQ ID NO: 8, and a heavy chain comprising the amino acid sequence of SEQ ID NO: 10.

In a preferred embodiment, the anti-HIV-1 antibody comprises a light chain comprising the amino acid sequence of SEQ ID NO: 8, and a heavy chain comprising the amino acid sequence of SEQ ID NO: 11.

In a preferred embodiment, the anti-HIV-1 antibody comprises a light chain comprising the amino acid sequence of SEQ ID NO: 8, and a heavy chain comprising the amino acid sequence of SEQ ID NO: 12.

In a preferred embodiment, the anti-HIV-1 antibody comprises a light chain comprising the amino acid sequence of SEQ ID NO: 9, and a heavy chain comprising the amino acid sequence of SEQ ID NO: 10.

In a preferred embodiment, the anti-HIV-1 antibody comprises a light chain comprising the amino acid sequence of SEQ ID NO: 9, and a heavy chain comprising the amino acid sequence of SEQ ID NO: 11.

In a preferred embodiment, the anti-HIV-1 antibody comprises a light chain comprising the amino acid sequence of SEQ ID NO: 9, and a heavy chain comprising the amino acid sequence of SEQ ID NO: 12.

In other preferred embodiments, the light chain of the anti-HIV-1 antibody may have about 70%, 75%, 80%, 85%, 90%, 91%, 92%, 93%, 94%, 95%, 96%, 97%, 98%, 99% or more homology to the amino acid sequence consisting of SEQ ID NO: 7, SEQ ID NO: 8, or SEQ ID NO: 9 and the heavy chain of the anti-HIV-1 antibody may have about 70%, 75%, 80%, 85%, 90%, 91%, 92%, 93%, 94%, 95%, 96%, 97%, 98%, 99% or more homology to the amino acid sequence consisting of SEQ ID NO: 10, SEQ ID NO: 11, or SEQ ID NO: 12.

In one embodiment described herein, the anti-HIV-1 antibody comprises a light chain comprising the amino acid sequence selected from the group consisting of SEQ ID NO: 1, SEQ ID NO: 2, or SEQ ID NO: 3 and a heavy chain comprising the amino acid sequence selected from the group consisting of SEQ ID NO: 4, SEQ ID NO: 5, or SEQ ID NO: 6.

In a preferred embodiment, the anti-HIV-1 antibody comprises a light chain comprising the amino acid sequence of SEQ ID NO: 1, and a heavy chain comprising the amino acid sequence of SEQ ID NO: 4.

In a preferred embodiment, the anti-HIV-1 antibody comprises a light chain comprising the amino acid sequence of SEQ ID NO: 1, and a heavy chain comprising the amino acid sequence of SEQ ID NO: 5.

In a preferred embodiment, the anti-HIV-1 antibody comprises a light chain comprising the amino acid sequence of SEQ ID NO: 1, and a heavy chain comprising the amino acid sequence of SEQ ID NO: 6.

In a preferred embodiment, the anti-HIV-1 antibody comprises a light chain comprising the amino acid sequence of SEQ ID NO: 2, and a heavy chain comprising the amino acid sequence of SEQ ID NO: 4.

In a preferred embodiment, the anti-HIV-1 antibody comprises a light chain comprising the amino acid sequence of SEQ ID NO: 2, and a heavy chain comprising the amino acid sequence of SEQ ID NO: 5.

In a preferred embodiment, the anti-HIV-1 antibody comprises a light chain comprising the amino acid sequence of SEQ ID NO: 2, and a heavy chain comprising the amino acid sequence of SEQ ID NO: 6.

In a preferred embodiment, the anti-HIV-1 antibody comprises a light chain comprising the amino acid sequence of SEQ ID NO: 3, and a heavy chain comprising the amino acid sequence of SEQ ID NO: 4.

In a preferred embodiment, the anti-HIV-1 antibody comprises a light chain comprising the amino acid sequence of SEQ ID NO: 3, and a heavy chain comprising the amino acid sequence of SEQ ID NO: 5.

In a preferred embodiment, the anti-HIV-1 antibody comprises a light chain comprising the amino acid sequence of SEQ ID NO: 3, and a heavy chain comprising the amino acid sequence of SEQ ID NO: 6.

In other preferred embodiments, the light chain of the anti-HIV-1 antibody may have about 70%, 75%, 80%, 85%, 90%, 91%, 92%, 93%, 94%, 95%, 96%, 97%, 98%, 99% or more homology to the amino acid sequence consisting of SEQ ID NO: 1, SEQ ID NO: 2, or SEQ ID NO: 3, and the heavy chain of the anti-HIV-1 antibody may have about 70%, 75%, 80%, 85%, 90%, 91%, 92%, 93%, 94%, 95%, 96%, 97%, 98%, 99% or more homology to the amino acid sequence consisting of SEQ ID NO: 4, SEQ ID NO: 5, or SEQ ID NO: 6.

In some preferred embodiments, the anti-HIV-1 antibodies of the present invention specifically bind to HIV-1 p24 protein. In some embodiments, the anti-HIV-1 antibodies of the present invention bind to an epitope of HIV-1 p24 protein. In some preferred embodiments, the anti-HIV-1 antibodies of the present invention bind to a linear epitope of HIV-1 p24 protein. In some preferred embodiments, the anti-HIV-1 antibodies of the present invention bind to a linear epitope comprising at least five contiguous amino acids selected from the amino acid sequence of HIV-1 p24 protein (SEQ ID NO: 35) or a sequence having at least 90% homology with said sequence. In other embodiments, the amino acid sequence of HIV-1 p24 protein is set forth in SEQ ID NO: 36.

In other preferred embodiments, the anti-HIV-1 antibodies of the present invention bind to an epitope of HIV-1 p24 protein characterized in that said epitope comprises the amino acid sequence of SEQ ID NO: 33.

In more preferred embodiments, the anti-HIV-1 antibodies of the present invention bind to an epitope of HIV-1 p24 protein characterized in that said epitope comprises an amino acid sequence selected from the group consisting of SEQ ID NO: 33, and wherein said antibody comprises a light chain comprising complementary determining regions L-CDR1, L-CDR2 and L-CDR3, wherein the amino acid sequence of L-CDR1 is selected from the group consisting of SEQ ID NO: 15, SEQ ID NO: 18 and SEQ ID NO: 21, the amino acid sequence of L-CDR2 is selected from the group consisting of SEQ ID NO: 16, SEQ ID NO: 19 and SEQ ID NO: 22, and the amino acid sequence of L-CDR3 is selected from the group consisting of SEQ ID NO: 17, SEQ ID NO: 20 and SEQ ID NO: 23, and further comprise a heavy chain comprising complementary determining regions H-CDR1, H-CDR2 and H-CDR3, wherein the amino acid sequence of H-CDR1 is selected from the group consisting of SEQ ID NO: 24, SEQ ID NO: 27 and SEQ ID NO: 30, the amino acid sequence of H-CDR2 is selected from the group consisting of SEQ ID NO: 25, SEQ ID NO: 28 and SEQ ID NO: 31, and the amino acid sequence of H-CDR3 is selected from the group consisting of SEQ ID NO: 26, SEQ ID NO: 29 and SEQ ID NO: 32.

In some preferred embodiments, the anti-HIV-1 antibodies of the present invention bind to an epitope of HIV-1 p24 protein characterized in that said epitope comprises the amino acid sequence of SEQ ID NO: 33, and wherein said antibody comprises a light chain comprising complementary determining regions L-CDR1, L-CDR2 and L-CDR3, wherein the amino acid sequence of L-CDR1 is SEQ ID NO: 18, the amino acid sequence of L-CDR2 is SEQ ID NO: 19, and the amino acid sequence of L-CDR3 is SEQ ID NO: 20, and further comprise a heavy chain comprising complementary determining regions H-CDR1, H-CDR2 and H-CDR3, wherein the amino acid sequence of H-CDR1 is SEQ ID NO: 27, the amino acid sequence of H-CDR2 is SEQ ID NO: 28, and the amino acid sequence of H-CDR3 is SEQ ID NO: 29.

In some embodiments, the anti-HIV-1 antibody of the present invention is bound to a solid support.

D. Affinity Tags

An anti-HIV-1 antibody according to the present invention may optionally include an affinity tag. Affinity tags are useful for purification. Exemplary affinity tags include polyhistidine, Glutathione S-transferase (GST), chitin binding protein, maltose binding protein (MBP), streptavidin binding peptide (Strep-tag), isopeptide bond forming, FLAG-tag, V5-tag, Myc-tag, HA-tag, NE-tag, AviTag, Calmodulin-tag, polyglutamate, S-tag, SBP-tag, Softag 1, Softag 3, TC tag, VSV-tag, Xpress tag, Isopeptag, SpyTag, SnoopTag, biotin carboxyl carrier protein, green fluorescent protein-tag, HaloTag, Nus-tag, and thioredoxin-tag, although the choice of affinity tag is not particularly limiting.

A anti-HIV-1 antibody may nevertheless lack an affinity tag, for example, if the affinity tag is removed after use or if the antibody is purified using a strategy that does not require an affinity tag. An exemplary affinity tag is polyhistidine, which typically includes an amino acid sequence comprising between 4 and 10 consecutive histidines.

The anti-HIV-1 antibodies of the present invention may optionally include an affinity tag and may optionally be purified using said affinity tag. Several methods of purification of anti-HIV-1 antibodies are available in the state of the art and the skilled person is well aware of them. Exemplary methods of purification for anti-HIV-1 antibodies, comprising or not an affinity tags, are immobilized metal affinity chromatography (IMAC), Protein A/G affinity, exchange chromatography (IEX or IEC), hydrophobic interaction chromatography (HIC) and/or additional use of tags and affinity chromatography techniques beyond IMAC or Protein A/G. The purification method and tags utilized should not be considered limiting.

II. Nucleic Acids, Cloning Cells, and Expression Cells

The present invention also relates to nucleic acids comprising a nucleotide sequence encoding the anti-HIV-1 antibodies described herein. The nucleic acid may be an isolated nucleic acid. The nucleic acid may be DNA or RNA. DNA comprising a nucleotide sequence encoding an anti-HIV-1 antibody described herein typically comprises a promoter that is operably-linked to the nucleotide sequence. The promoter is preferably capable of driving constitutive or inducible expression of the nucleotide sequence in an expression cell of interest. Said nucleic acid may also comprise a selectable marker useful to select the cell containing said nucleic acid of interest. Useful selectable markers are well known by the skilled person. The precise nucleotide sequence of the nucleic acid is not particularly limiting so long as the nucleotide sequence encodes an anti-HIV-1 antibody described herein. Codons may be selected, for example, to match the codon bias of an expression cell of interest (e.g., a mammalian cell such as a human cell) and/or for convenience during cloning. DNA may be a plasmid, for example, which may comprise an origin of replication (e.g., for replication of the plasmid in a prokaryotic cell).

In one embodiment described herein, the nucleic acid comprises a nucleotide sequence encoding the anti-HIV-1 antibody of the present invention, a promoter operably linked to the nucleotide sequence and a selectable marker.

In some preferred embodiments, the nucleic acid comprises the nucleotide sequence selected from the group consisting of SEQ ID NO: 37, SEQ ID NO: 38, SEQ ID NO: 39, SEQ ID NO: 40, SEQ ID NO: 41 and SEQ ID NO: 42. In more preferred embodiments, the nucleic acid of the light chain of the anti-HIV-1 antibody of the present invention comprises the nucleotide sequence selected from the group consisting of SEQ ID NO: 37, SEQ ID NO: 39, and SEQ ID NO: 41, and the nucleic acid of the heavy chain of the anti-HIV-1 antibody of the present invention comprises the nucleotide sequence selected from the group consisting of SEQ ID NO: 38, SEQ ID NO: 40 and SEQ ID NO: 42.

In some embodiments, the nucleic acid of the light and heavy chains of the anti-HIV-1 antibody of the present invention comprises respectively the nucleotide sequence of SEQ ID NO: 37 and the nucleotide sequence of SEQ ID NO: 38. In other embodiments, the nucleic acid of the light and heavy chains of the anti-HIV-1 antibody of the present invention comprises respectively the nucleotide sequence of SEQ ID NO: 39 and the nucleotide sequence of SEQ ID NO: 40. In other embodiments, the nucleic acid of the light and heavy chains of the anti-HIV-1 antibody of the present invention comprises respectively the nucleotide sequence of SEQ ID NO: 41 and the nucleotide sequence of SEQ ID NO: 42.

Various aspects of the present invention also relate to a cell comprising a nucleic acid comprising a nucleotide sequence that encodes an anti-HIV-1 antibody as described herein. The cell may be an expression cell or a cloning cell. Nucleic acids are typically cloned in *E. coli*, although other cloning cells may be used.

If the cell is an expression cell, the nucleic acid is optionally a nucleic acid of a chromosome, i.e., wherein the nucleotide sequence is integrated into the chromosome, although the nucleic acid may be present in an expression cell, for example, as extrachromosomal DNA or vectors, such as plasmids, cosmids, phages, etc. The format of the vector should not be considered limiting.

In one embodiment described herein, the cell is typically an expression cell. The nature of the expression cell is not particularly limiting. Mammalian expression cells may allow for favorable folding, post-translational modifications, and/or secretion of a recombinant antibody or oligomeric recombinant antibody, although other eukaryotic cells or prokaryotic cells may be used as expression cells. Exemplary expression cells include CHO cell lines, such as TunaCHO or ExpiCHO, Expi293, BHK, NSO, Sp2/0, COS, C127, HEK, HT-1080, PER.C6, HeLa, and Jurkat cells. The cell may also be selected for integration of a vector, more preferably for integration of a plasmid DNA.

The anti-HIV-1 antibodies of the present invention can be produced by appropriate transfection strategy of the nucleic acids comprising a nucleotide sequence that encodes the anti-HIV-1 antibodies into mammalian cells. The skilled person is aware of the different techniques available for transfection of nucleic acids into the cell line of choice (lipofection, electroporation, etc). Thus, the choice of the mammalian cell line and transfection strategy should not be considered limiting. The cell line could be further selected for integration of the plasmid DNA.

In one preferred embodiment described herein, the cell comprises the anti-HIV-1 antibody of the present invention.

III. Compositions and kits

Various aspects of the present invention relate to compositions comprising an anti-HIV-1 antibody as described herein.

In one embodiment described herein, the composition comprises the anti-HIV-1 antibody of the present invention and a solid support.

In other embodiment, the composition comprises the anti-HIV-1 antibody of the present invention and a solid support, wherein the anti-HIV-1 antibody is covalently or non-covalently bound to the solid support. The term "non-covalently bound," as used herein, refers to specific binding such as between an antibody and its antigen, a ligand and its receptor, or an enzyme and its substrate, exemplified, for example, by the interaction between streptavidin binding protein and streptavidin or an antibody and its antigen.

In other embodiment, the composition comprises the anti-HIV-1 antibody of the present invention and a solid support, wherein the anti-HIV-1 antibody is directly or indirectly bound to a solid support. The term "direct" binding, as used herein, refers to the direct conjugation of a molecule to a solid support, e.g., a gold-thiol interaction that binds a cysteine thiol of an anti-HIV-1 antibody to a gold surface. The term "indirect" binding, as used herein, includes the specific binding of an anti-HIV-1 antibody to another molecule that is directly bound to a solid support, e.g., an anti-HIV-1 antibody may bind an antibody that is directly bound to a solid support thereby indirectly binding the anti-HIV-1 antibody to the solid support. The term "indirect" binding is independent of the number of molecules between the anti-HIV-1 antibody and the solid support so long as (a) each interaction between the daisy chain of molecules is a specific or covalent interaction and (b) a terminal molecule of the daisy chain is directly bound to the solid support.

A solid support may comprise a particle, a bead, a membrane, a surface, a polypeptide chip, a microtiter plate, or the solid-phase of a chromatography column. Preferably, the solid support may be a latex bead.

A composition may comprise a plurality of beads or particles, wherein each bead or particle of the plurality of beads or particles are directly or indirectly bound to at least one anti-HIV-1 antibody as described herein. A composition may comprise a plurality of beads or particles, wherein each bead or particle of the plurality of beads or particles are covalently or non-covalently bound to at least one anti-HIV-1 antibody as described herein.

Various aspects of the embodiments relate to a kit for detecting the presence of HIV-1 in a sample, said kit comprising at least one anti-HIV-1 antibody and a solid support or composition as described herein. In some embodiments, the at least one antibody is covalently or non-covalently bound to a solid support.

The anti-HIV-1 antibodies, compositions and kits described herewith can be for use, for example, in assays for detecting the presence of HIV-1 in a sample or for measuring the concentration of HIV-1 in a sample, but they are not limited to said assays. The anti-HIV-1 antibodies, compositions and kits of the present invention can also be used for detection of HIV-1 only or in combination with other antibodies for detection of other pathogens, such as multiplex assays and methods.

In some preferred embodiments, the anti-HIV-1 antibodies of the present invention are used in methods and assays in which other RNA viruses are also detected. In other embodiments, said anti-HIV-1 antibodies and other anti-HIV-2 antibodies are used in methods and assays for simultaneous detection of HIV-1 and HIV-2 in a sample. In more preferred embodiments, said anti-HIV-1 antibodies and other anti-HIV-2 antibodies are used in methods and assays for specific detection of HIV-1 p24 protein and HIV-2 p26 protein in a sample.

It is also contemplated within the scope of the present invention the use of more than one anti-HIV-1 antibodies as described herein in methods and assays for detection of HIV-1 in a sample.

Hereinafter, the present invention is described in more detail with reference to illustrative examples, which does not constitute a limitation of the present invention.

EXEMPLIFICATION

Example 1: Preferred Anti-HIV-Antibodies and Stable Cell Line Production

Specific combination of the light and heavy chains of the present invention resulted in preferred antibodies, as disclosed herein:

TABLE 1

Preferred combination of light and heavy chains of anti-HIV-1 antibodies

| Antibody | Light chain | Heavy Chain |
|---|---|---|
| #A | SEQ ID NO: 1 | SEQ ID NO: 4 |
| #B | SEQ ID NO: 2 | SEQ ID NO: 5 |
| #D | SEQ ID NO: 3 | SEQ ID NO: 6 |

The variable and constant regions for each antibody were cloned into a bicistronic vector and expressed in Chinese hamster ovary (CHO) cells. Manufacturing characteristics for each antibody were evaluated based on the capability to generate stable cell line clones for each one, as well as the reproducible expression and purification of functional antibodies.

Pool Development

Transfection: Expression of three constructs containing the nucleotides sequences for antibodies #A, #B and #D (SEQ ID NOs: 37 to 42) were generated in a bicistronic expression vector containing the heavy chain and light chain of each antibody. To express the antibodies, CHO cells were electroporated with 200 μg of DNA to create stable cell lines. Twenty-four hours later, the transfected cells were counted and placed under selection media for stable integration of the protein genes.

Pool Generation: The transfected cells were seeded into selection media at a cell density of $0.5\times10^6$ cells/mL in a 250 mL shaker flask with 50 mL working volume and incubated at 37° C. with 5% CO2. During the selection process the cells were spun down and resuspended in fresh selection media every 2-3 days until the pool recovered its growth rate and viability. The cell culture was monitored for growth, via viable cell density (VCD) and percent viability, and titer.

Production Pool: One liter production runs were performed from stable pools to evaluate the VVD, titer, and viability. The cells were scaled up in production media in 3 L shake flasks (1 L working volume). The conditioned media supernatant harvested from each stable pool production run was clarified by centrifuge spinning and protein was purified by affinity purification using a Protein A column (Tables 2-4).

Cell Line Banking: Cells were grown to $2.5\times10^6$ cells per mL. At the time of harvest for cell banking, the viability was above 95%. The cells were then centrifuged, and the cell pellet was resuspended in CHO complete media with 7.5% dimethylsulfoxide (DMSO) (Sigma-Aldrich, D1435) to a cell count of $15\times10^6$ cells per mL per vial. Five total vials of each of the pools were produced and cryopreserved for storage in liquid nitrogen.

TABLE 2

Production and purification for antibody #A pools 1 and 2.

| Antibody #A | Step of stable pool evaluation | Pool 1 | Pool 2 |
|---|---|---|---|
| Cell culturing | Duration of Production Run | 17 days | 15 days |
| | Expression titer at harvest | 9 mg/L | 2.63 mg/L |
| Purification | Volume of load onto purification resin | 1 L | 1 L |
| | Yield obtained from purification | 8.45 mg | 3.85 mg |
| | Purification titer | 8.45 mg/L | 4.13 mg/L |

TABLE 3

Production and purification process for antibody #B pools 1 and 2.

| Antibody #B | Step of stable pool evaluation | Pool 1 | Pool 2 |
|---|---|---|---|
| Cell culturing | Duration of Production Run | 18 days | 15 days |
| | Expression titer at harvest | 209 mg/L | 1.9 mg/L |
| Purification | Volume of load onto purification resin | 1 L | 1 L |
| | Yield obtained from purification | 97.74 mg | 0.88 mg |
| | Purification titer | 97.74 mg/L | 1.16 mg/L |

TABLE 4

Production and purification process for antibody #D pools 1 and 2.

| Antibody #D | Step of stable pool evaluation | Pool 1 | Pool 2 |
|---|---|---|---|
| Cell culturing | Duration of Production Run | 18 days | 17 days |
| | Expression titer at harvest | 34.4 mg/L | 4.15 mg/L |
| Purification | Volume of load onto purification resin | 1 L | 1 L |
| | Yield obtained from purification | 84.45 mg | 5.70 mg |
| | Purification titer | 84.45 mg/L | 6.71 mg/L |

Stable Antibody Generation

Figure 2:
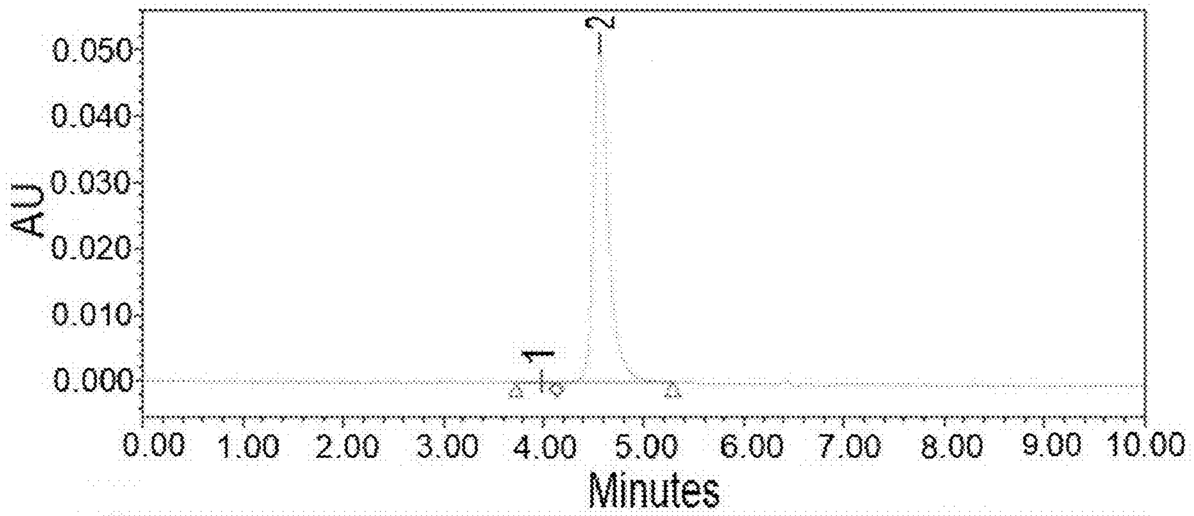
FIG. 2. SE-UPLC analysis % monomer for antibody #B and SDS-PAGE for antibody #B single clones (lanes 1, 2 and 3 represent subclones ran in reducing and non-reducing conditions, respectively).
Figure 2:
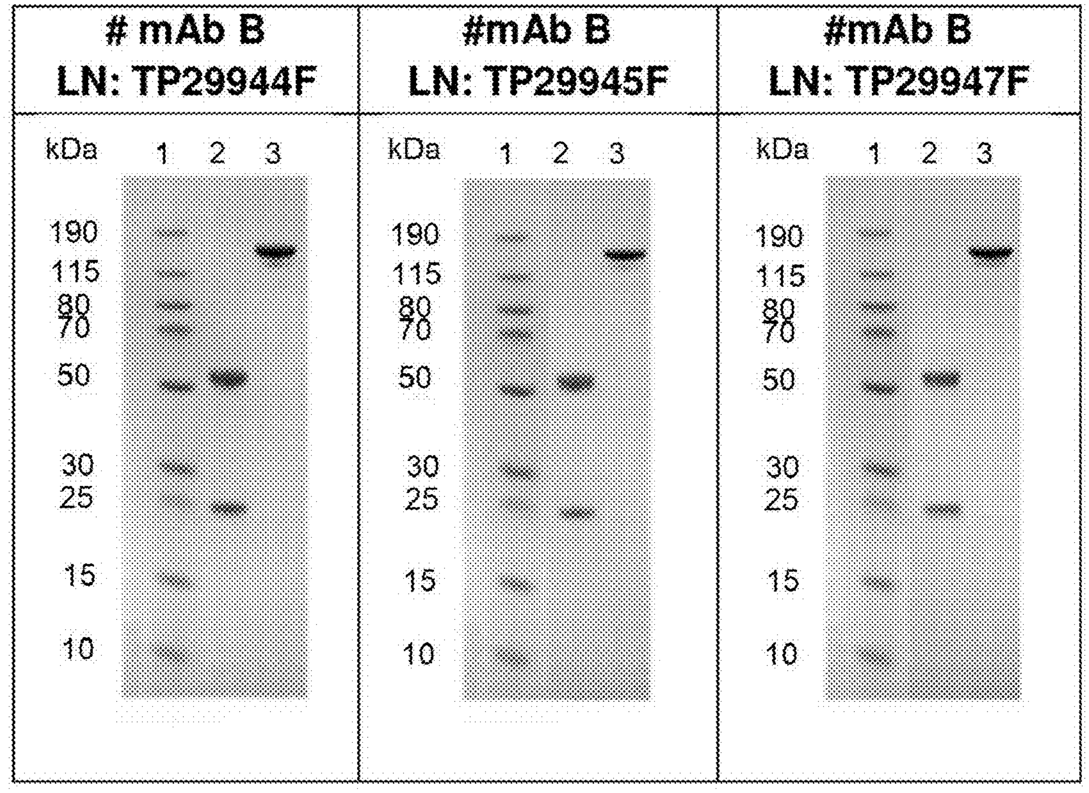
Figure 3:
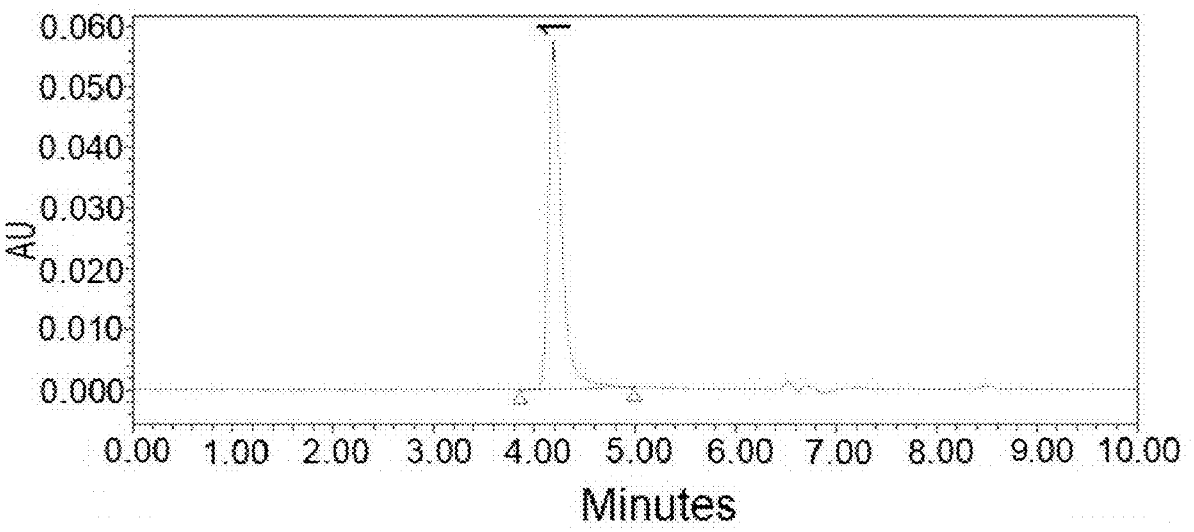
FIG. 3. SE-UPLC analysis % monomer for antibody #D and SDS-PAGE for antibody #D single clones (lanes 1, 2 and 3 represent subclones ran in reducing and non-reducing conditions, respectively).
Figure 3:
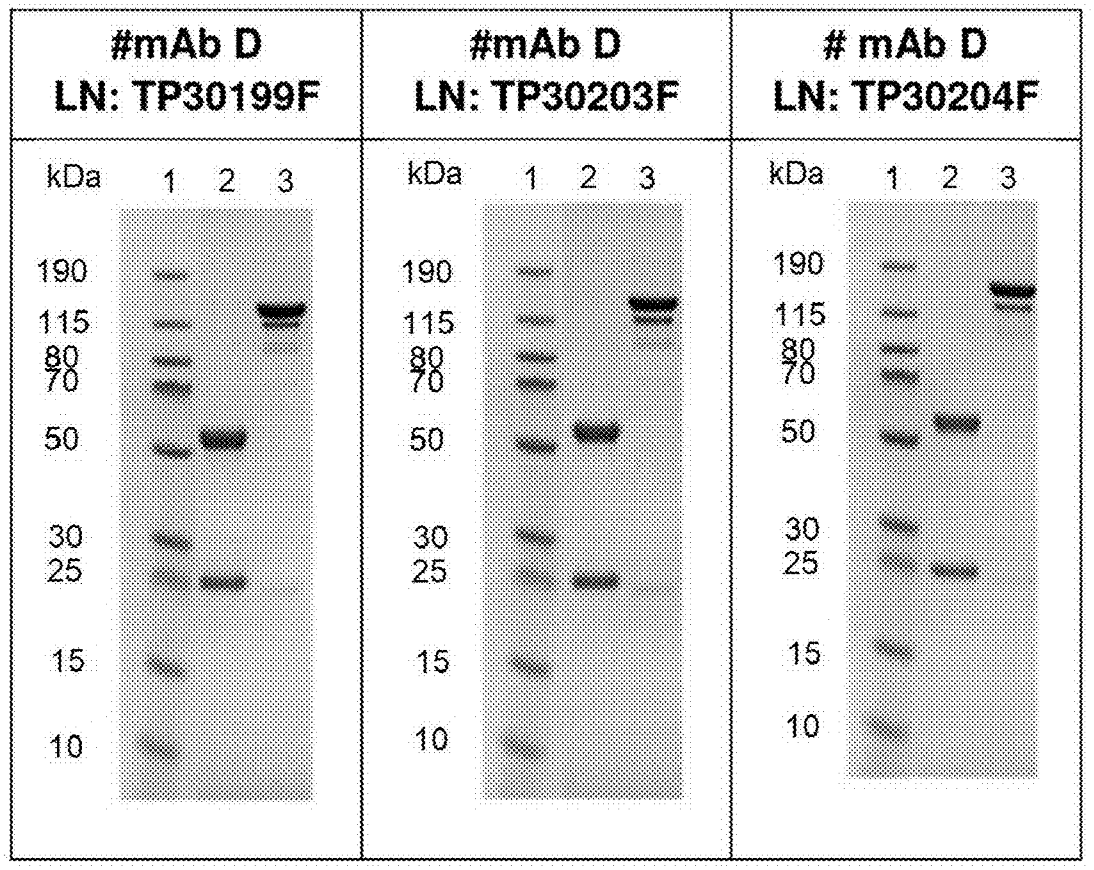

Starting from the best banked pool cell line for antibodies #A, #B and #D, stable clones were obtained via single cell cloning. The best clones for each antibody were selected based on expression level and the bioanalytical characterization of purified material for antibodies #A, #B and #D from the production runs. The bioanalytical characterization included SE-UPLC and SDS-PAGE (FIGS. 1-3).

Example 2: Antibody Modelling and Evaluation

Figure 4:
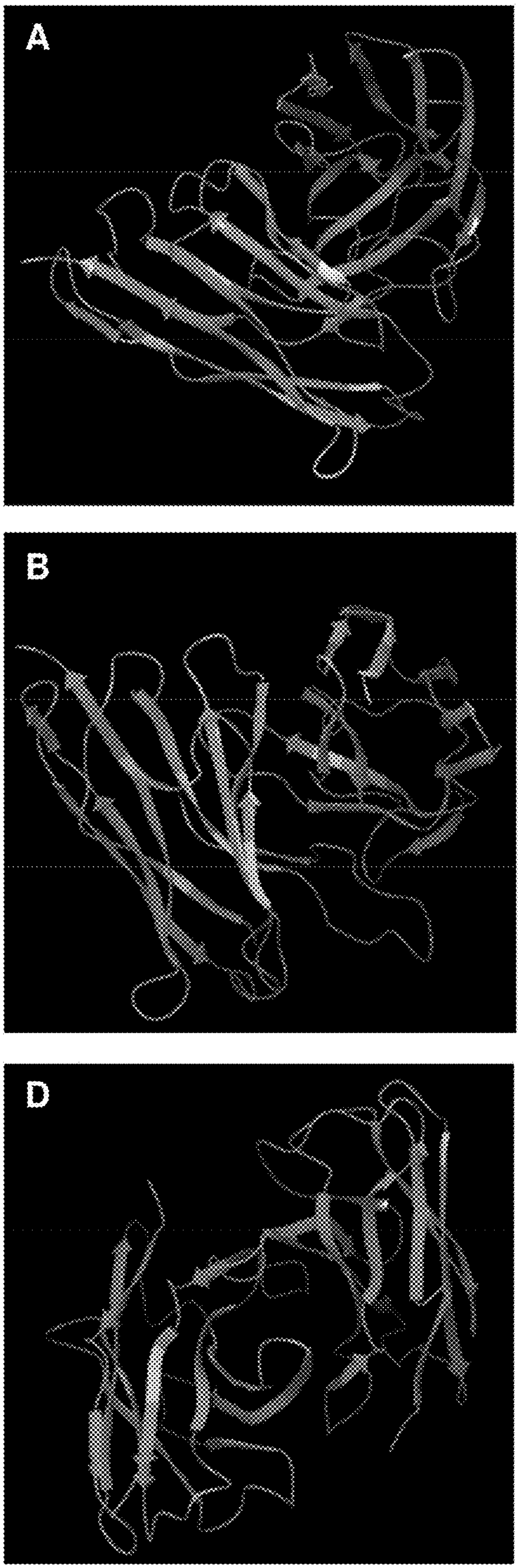
FIG. 4. PDB predicted structure for antibodies #A, #B and #D (4A, 4B and 4D respectively). For antibody #A the PDB structure code 2XKN was used in the homology query, while codes 5OPY and 1F3D were used respectively for antibodies B #and #D, respectively.
Figure 5:
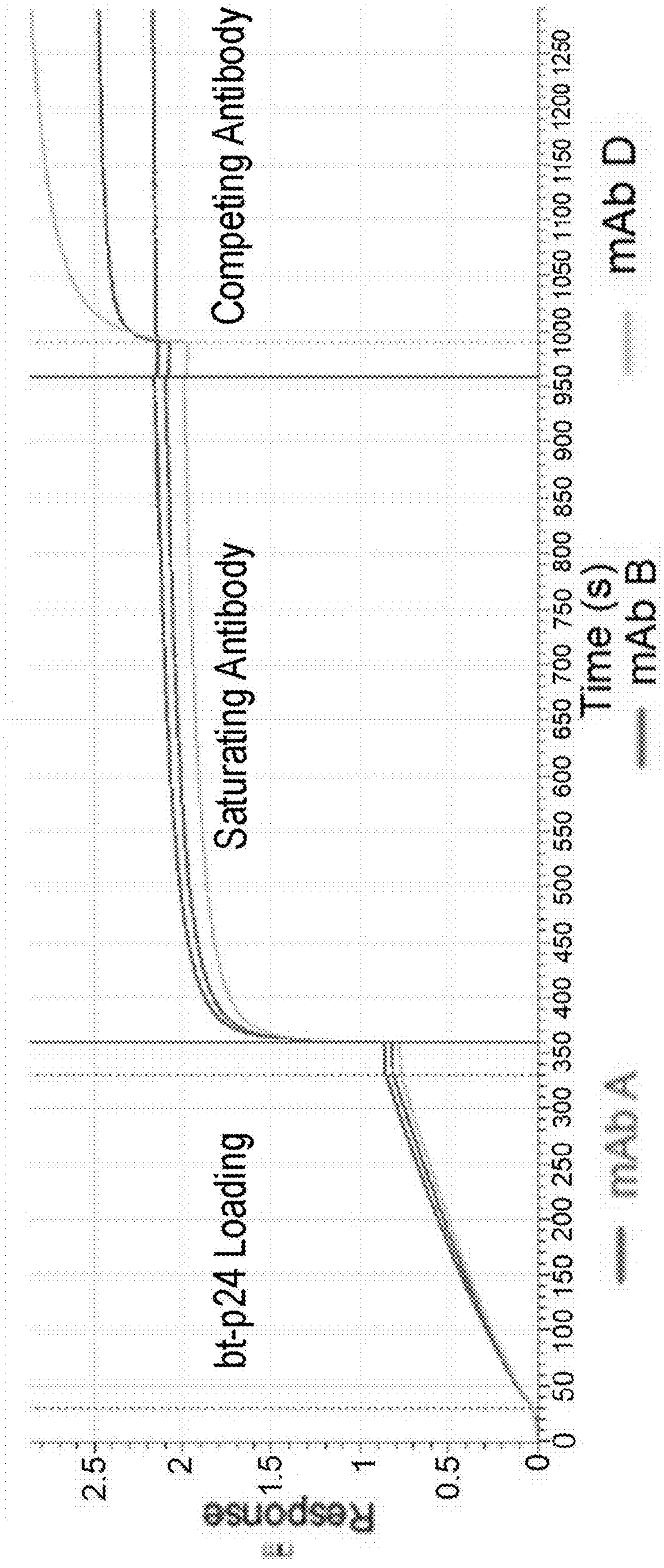
FIG. 5. Sensorgram of saturating antibody #A versus competing #B and #D. Antibodies #B and #D add signal to #A demonstrating these antibodies do not compete for binding within the same epitope region.
Figure 6:
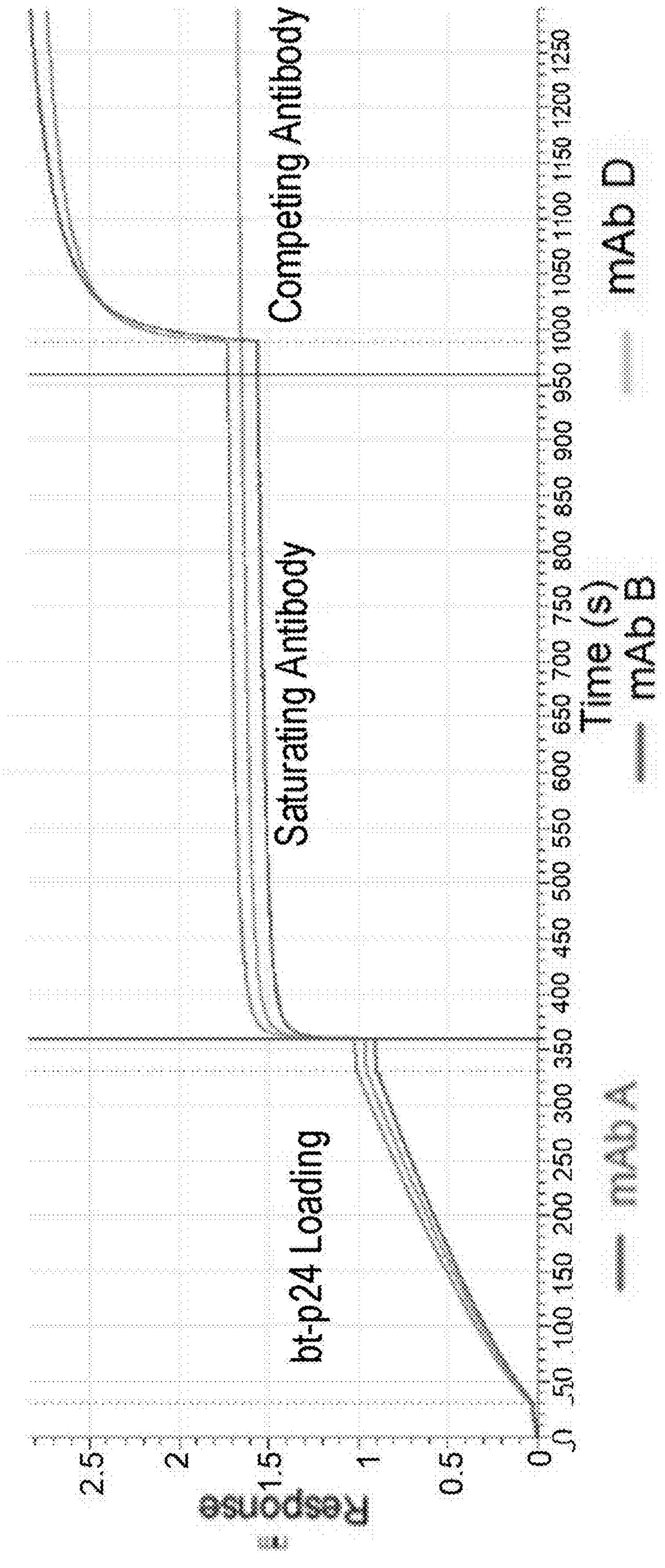
FIG. 6. Sensorgram of saturating antibody #B versus competing #A and #D. Antibodies #A and #D add signal to #B demonstrating that these antibodies do not compete for binding within the same epitope region.
Figure 7:
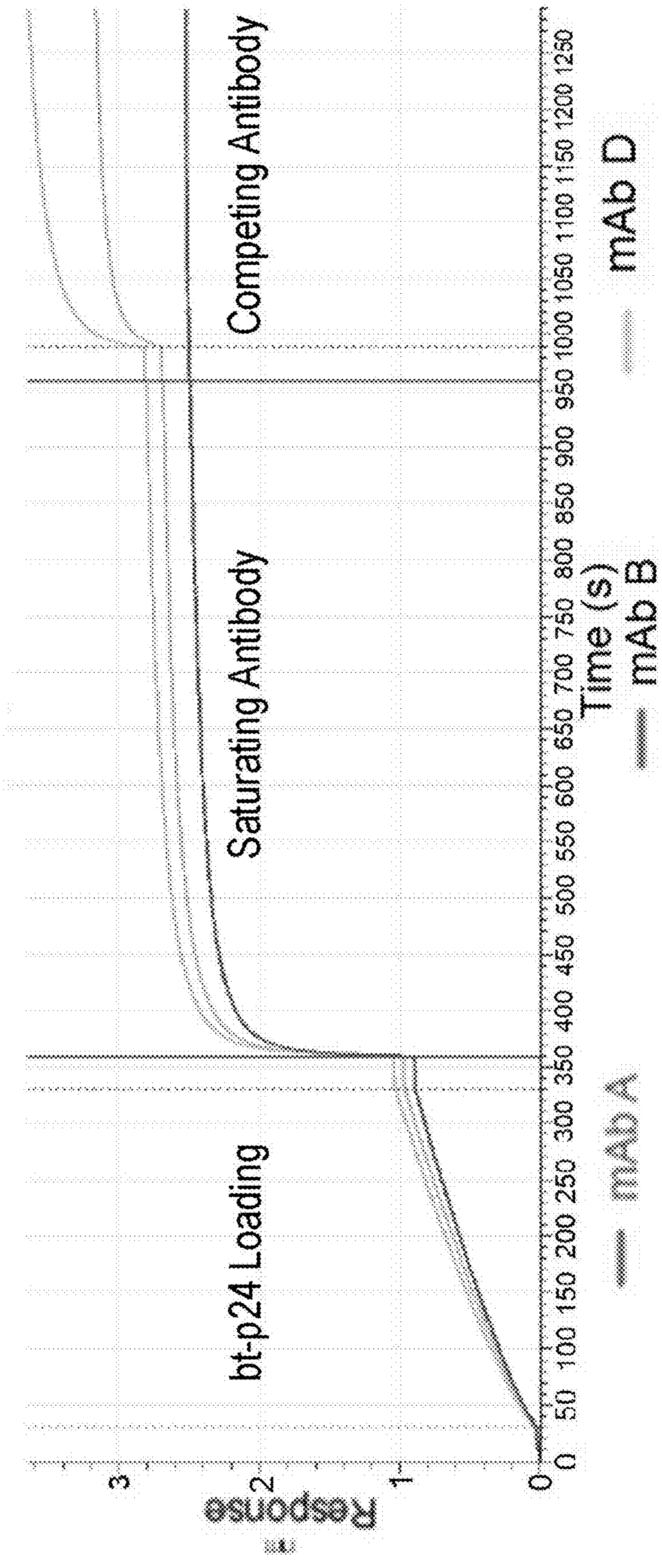
FIG. 7. Sensorgram of saturating antibody #D versus competing #A and #B. Antibodies #A and #B add signal to #D demonstrating that these antibodies do not compete for binding within the same epitope region.
Figure 8:
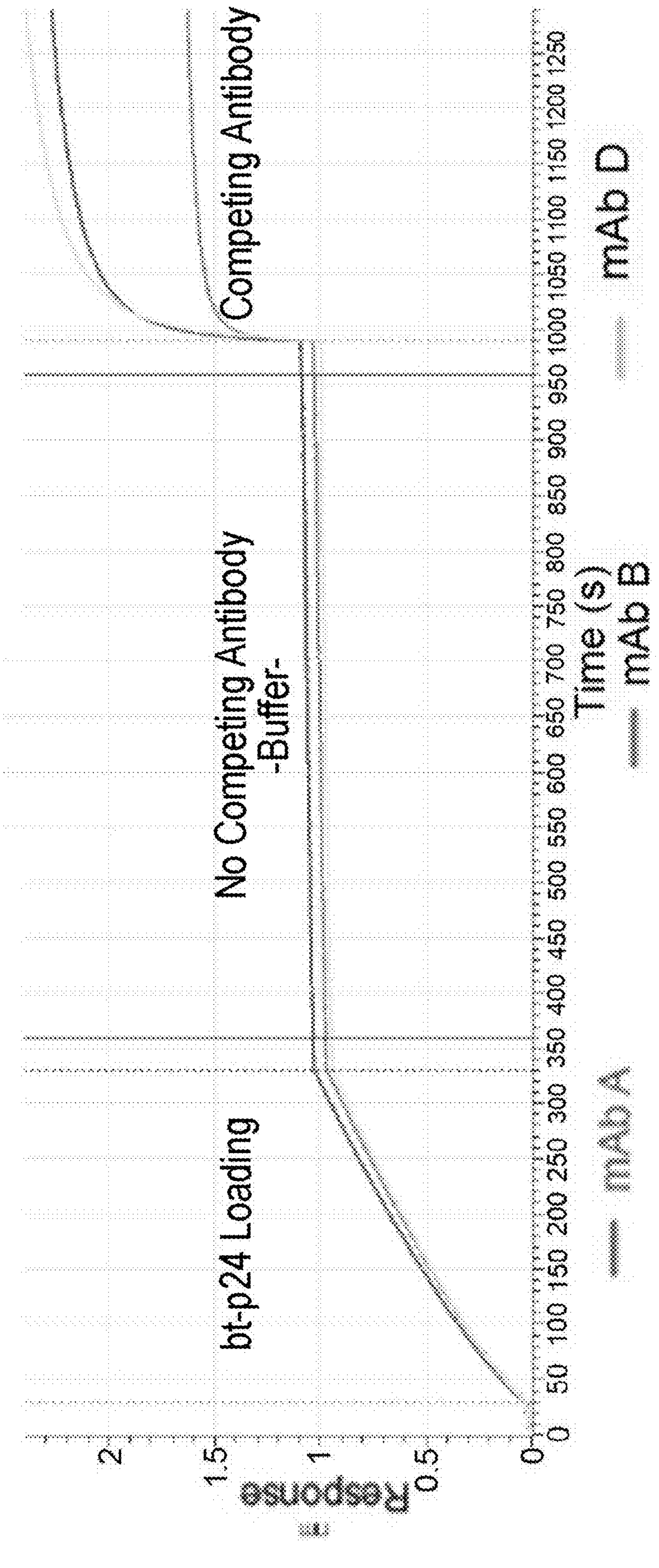
FIG. 8 Sensorgram of antibodies #A, #B and #D association to HIV-1 p24 in the absence of competing antibody. Each antibody attains its full binding signal (experimental control).

A three-dimensional structure model of antibodies #A, #B and #D was built by antibody homology using the computational and modelling software Bioiluminate (Schrodinger), version 3.5. Briefly, the amino acid sequences for the VH and VL regions of antibodies #A, #B and #D were loaded to Bioiluminate. Framework regions and CDRs were identified through searching the antibody structures in the Protein Data Bank (PDB) and selecting a PDB template based on high sequence similarity and structural fitness (Table 5). The predicted CDR sequences for each of the antibodies of the present invention are shown in Table 5 and the PDB predicted structure are shown in FIGS. 4A, 4B and 4D respectively for antibody #A, #B and #D. For antibody #A the PDB structure code 2XKN was used in the homology query, while codes 5OPY and 1F3D were used respectively for antibodies B #and #0.

Antibodies #A and #B resulted of the IgG1k isotype while antibody #0 resulted of the IgG2ak isotype.

TABLE 5

Chothia CDR sequences of the light and heavy chains of antibodies #A, #B and #D derived according to the Abysis database website.

| Antibody | CDR | Light chain | Heavy Chain |
|---|---|---|---|
| #A | CDR1 | RASQDISNYLH (SEQ ID NO: 15) | GFTFSSY (SEQ ID NO: 24) |
| | CDR2 | YTSRLHS (SEQ ID NO: 16) | TSGGN (SEQ ID NO: 25) |
| | CDR3 | QQGNSFPWT (SEQ ID NO: 17) | EVLSVPFAY (SEQ ID NO: 26) |
| #B | CDR1 | RASQSISDNLH (SEQ ID NO: 18) | GFAFSSY (SEQ ID NO: 27) |
| | CDR2 | YSSQSIS (SEQ ID NO: 19) | TSGVGN (SEQ ID NO: 28) |
| | CDR3 | QQSNSWPFT (SEQ ID NO: 20) | PPSYFGSSYDAMDY (SEQ ID NO: 29) |
| #D | CDR1 | RSSQSLVNSDGNTFLQ (SEQ ID NO: 21) | GYAFTSY (SEQ ID NO: 30) |
| | CDR2 | KVSNRFS (SEQ ID NO: 22) | DPYNGG (SEQ ID NO: 31) |
| | CDR3 | SQSTHVPWT (SEQ ID NO: 23) | PRWLPAGDY (SEQ ID NO: 32) |

Analysis of nucleotide sequences of the three antibodies show that all generated heavy (VH) and light chains (VL) have unique complementary determining regions (CDR) when queried against IgBLAST, an algorithm developed by the National Center for Biotechnology Information (NCBI) to facilitate analysis of immunoglobulin variable domain sequences against the ImMunoGeneTics Database (IMGT) database (Lefranc M-P. Lefranc G. IMGT® and 30 years of *Immunoinformatics Insight in Antibody V and C Domain Structure and Function*. In Jefferis R; Strohl W. R., Kato K. Antibodies 2019, vol. 8(29); 1-21).

Example 3: Epitope Mapping mAb D

The sequence of HIV-p24 was elongated by neutral GSGSGSG (SEQ ID NO: 43) linkers at the C- and N-terminus to avoid truncated peptides. The elongated antigen sequence was translated into linear 15 amino acid peptides with a peptide-peptide overlap of 14 amino acids. The resulting HIV-p24 peptide microarrays contained 232 different linear peptides printed in duplicate (464 spots) and were framed by additional HA (YPYDVPDYAG (SEQ ID NO: 44), 38 spots) and c-Myc (EQKLISEEDL (SEQ ID NO: 45), 38 spots) control peptides.

Washing Buffer: PBS, pH 7.4 with 0.05% Tween 20; washing for 3×10 sec after each incubation step Blocking Buffer: Rockland blocking buffer MB-070 (30 min before the first assay)

Incubation Buffer: Washing buffer with 10% blocking buffer

Assay Conditions: Antibody concentrations of 1 μg/ml, 10 μg/ml and 100 μg/ml in incubation buffer; incubation for 16 h at 4° C.; shaking at 140 rpm Secondary Antibody: Goat anti-mouse IgG (H+L) DyLight680 (0.2 μg/ml); 45 min staining in incubation buffer at RTControl Antibody: Mouse monoclonal anti-HA (12CA5) DyLight800 (0.5 μg/ml); 45 min staining in incubation buffer at RT Scanner: LI-COR Odyssey Imaging System; scanning offset 0.65 mm, resolution 21 μm, scanning intensities of 7/7 (red=680 nm/green=800 nm)

Pre-staining of a HIV-p24 peptide microarray was done with the secondary goat anti-mouse IgG (H+L) DyLight680 antibody in incubation buffer to investigate background interactions with the antigenderived peptides that could interfere with the main assays. Subsequent incubation of other HIV-p24 peptide microarray copies with monoclonal antibody D at concentrations of 1 μg/ml, 10 μg/ml and 100 μg/ml in incubation buffer was followed by staining with the secondary and control antibodies as well as read-out at scanning intensities of 7/7 (red/green). The additional HA peptides framing the peptide microarrays were subsequently stained as internal quality control to confirm the assay quality and the peptide microarray integrity.

Epitope mapping against HIV-p24 for mAb D, and a subsequent epitope substitution scan highlighted a conserved seven amino acid core motif PIAPGQM (SEQ ID NO:33).

Example 4: Epitope Binning Studies

Figure 9:
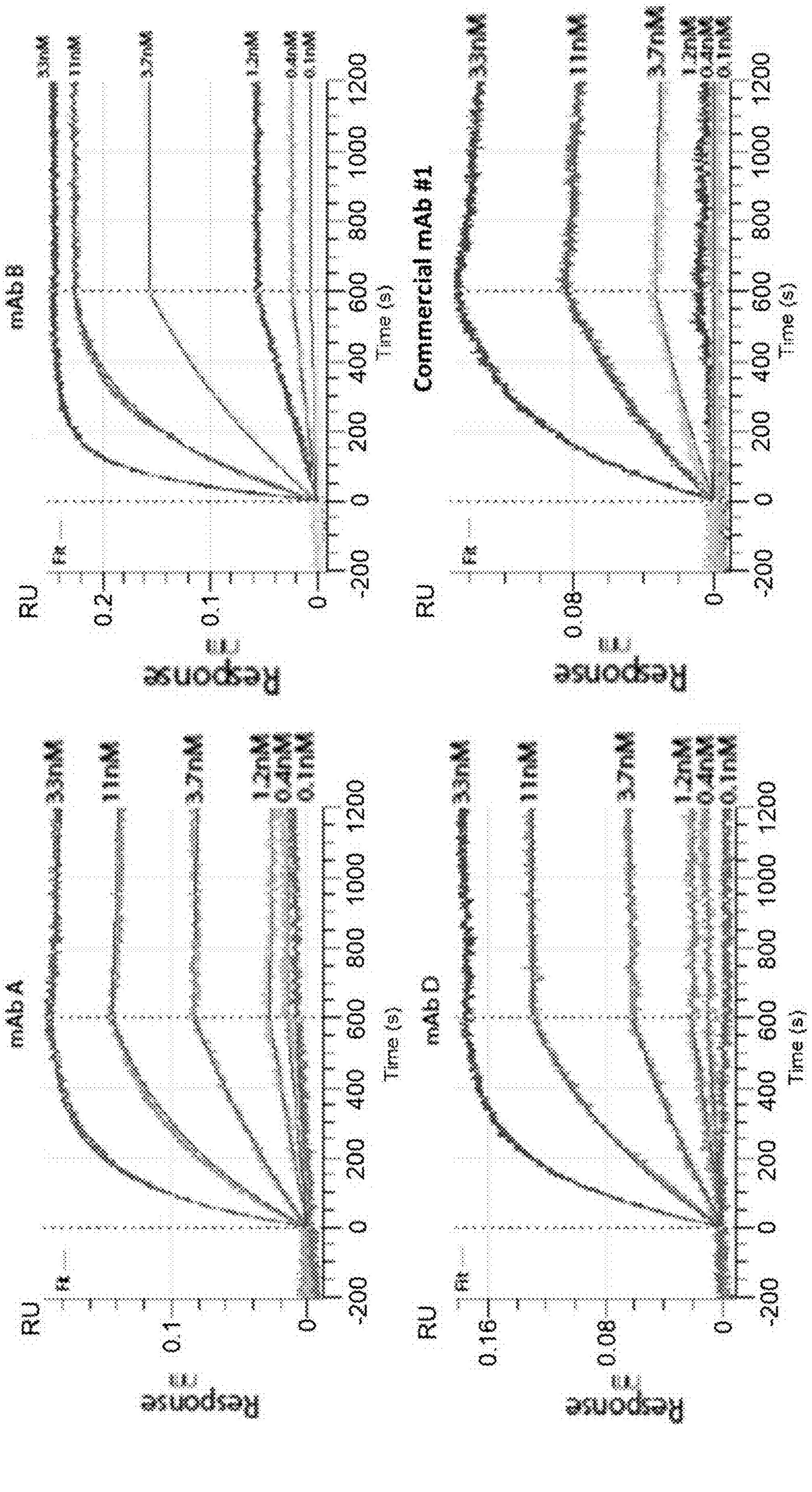
FIG. 9. Binding kinetics of antibodies #A, #B and #D and commercial mAb #1 to antigen HIV-1 p24 calculated by Biolayer Interferometry (BLI). Sensorgrams were performed for gradient concentrations of 0.1-33 nM and were fitted with a 1:1 binding model in order to calculate ka (association rate constant), kd (dissociation rate constant) and KD (equilibrium dissociation constant).
Figure 10:
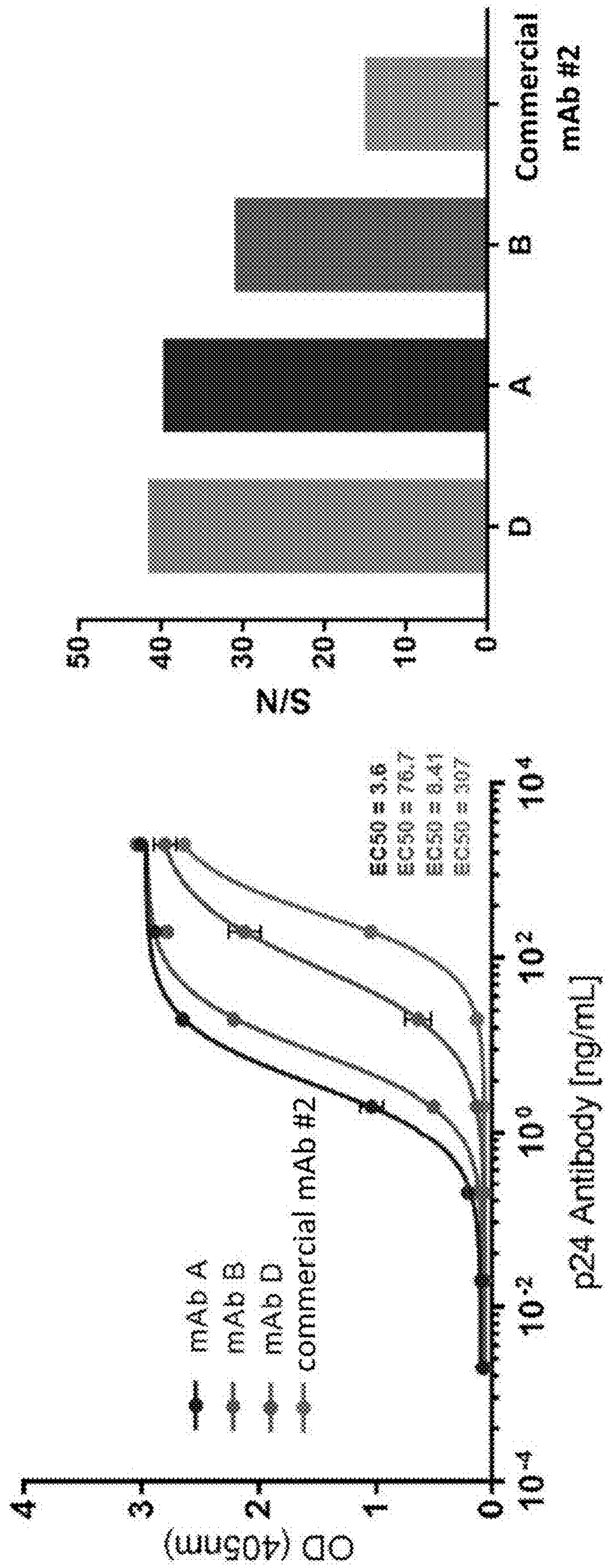
FIG. 10. Binding of antibodies #A, #B and #D and commercial mAb #2 to HIV-1 p24 capsid protein by indirect ELISA. Titration curves for each antibody start at a concentration of 2 μg/mL, with subsequent 1:10 dilutions (Left). Signal-to-noise data for an antibody concentration of 200 ng/mL is shown on the right, demonstrating poor performance of commercial mAb #2 when compared to antibodies #A, #B and #D.

The molecular docking and western blot evaluation of antibodies #A, #B and #D suggested that these antibodies recognize linear epitopes at regions 1, 4 and 7 respectively, of the HIV-1 p24 protein. To further confirm these observations, a tandem epitope binning assay was performed using Biolayer Interferometry (BLI). A yeast-derived version of HIV-1 p24 antigen was biotinylated (bt-p24) and loaded onto Streptavidin (SA) biosensors for 300 seconds. Loaded sensors were dipped into saturating antibody (100 μg/mL) for 600 seconds followed by competing antibody (25 μg/mL) for 300 seconds. The results show that when antibody #A binds to HIV-1 p24, antibodies #B and #D add an increase in the BLI signal response, demonstrating that antibodies #B and #D bind to distinct epitopes when compared to antibody A. Similarly, if antibodies #A or #D are used as saturating antibodies, the remainder antibodies do not show competition for the same epitope (FIG. 9-10).

Table 6 summarizes epitope binning data for antibodies #A, #B and #D. Briefly, the BLI signals for competing and saturating antibodies were normalized against the buffer. The threshold for determination of antibody blocking or binding was set at 0.02 so that self-blocking pairs could be recognized in the diagonal of the matrix (grey refers to binding and bold font to self-blocking).

PEARSON correlation coefficients were calculated against the first antibody #A using PEARSON function in Microsoft Excel (Liao-Chan S., et al., *Monoclonal Antibody Binding-site Diversity Assessment with a Cell-based Clustering Assay. Journal of Immunological Methods* 2014, vol. 405; 1-14). Three distinct bins were identified for antibodies #A, #B and #D. No antibody blocking was observed.

TABLE 6

Epitope binning matrix for anti-HIV-1 antibodies #A, #B and #D.

| | | Competing antibody | | | |
|---|---|---|---|---|---|
| | | #A | #B | #D | Pearson |
| Saturating antibody | #A | 0.019 | 0.663 | 0.625 | 1.000 |
| | #B | 0.854 | 0.025 | 0.899 | −0.506 |
| | #D | 0.697 | 0.778 | 0.008 | −0.357 |
| | Pearson | 1.000 | −0.522 | −0.041 | |

Example 5: Affinity Evaluation of Anti-HIV-1 Antibodies #a, #B and #D

To investigate in more detail the interaction between antibodies #A, #B and #D and the HIV-1 p24 antigen, affinity analysis by BLI was performed. Antibodies #A, #B and #D were compared with a commercial monoclonal antibody (commercial mAb #1). Anti-mouse Fc specific coated biosensors tips (ForteBio) were used to capture antibodies #A, #B and #D and commercial mAb #1. The gradient of concentrations used for each antibody ranged from 0.1 to 33 nM and each dilution was prepared in phosphate buffer (PBS) containing 0.01% (w/v) bovine serum albumin (BSA) and 0.02% (v/v) of detergent Tween-20. The recorded sensorgrams were fitted using a 1:1 binding model and the equilibrium constant KD was calculated from the ratio of the rate of dissociation and rate of association (kd/ka). The tested antibodies were ranked based on the calculated affinity constants as follows: antibody #B~antibody #D>antibody #A>commercial mAb #1. Although it was not possible to calculate an accurate KD value for antibodies #B and #D due to the long dissociation curves observed, the data presented shows that the calculated KD values for antibodies #A, #B and #D are lower than the value observed for the commercial mAb #1 (Table 7). This data supports the observation that antibodies #A, #B and #D display higher affinity to HIV-1 p24 than the commercial mAb #1.

TABLE 7

Binding of antibodies #A, #B, #D and commercial mAb #1to HIV-1 p24 protein by BLI.

| Antibody ID | $K_D$ (nM) | Ka (1/Ms) | Kd (1/s) | Rank | Full $R^2$ |
|---|---|---|---|---|---|
| A | 0.2 | $2.41 \times 10^5$ | $5.90 \times 10^{-5}$ | 2 | 0.9982 |
| B | $<2.4 \times 10^{-4}$ | $4.08 \times 10^5$ | $<1.0 \times 10^{-7}$ | 1 | 0.9993 |
| D | $<5.2 \times 10^{-4}$ | $1.94 \times 10^5$ | $<1.0 \times 10^{-7}$ | 1 | 0.9986 |
| (commercial mAb #1) | 1.3 | $1.28 \times 10^5$ | $1.62 \times 10^{-4}$ | 3 | 0.9974 |

$K_D$, equilibrium dissociation constant; Ka, association rate constant and Kd, dissociation rate constant.

Example 6: Binding Capacity of Anti-HIV-1 Antibodies #a, #B and #D

To further evaluate the binding of antibodies #A, #B and #D against HIV-1 p24 antigen, an indirect ELISA assay was completed. Titration curves were generated for each antibody using a starting concentration of 2 μg/mL and performing serial 1:10 dilutions until attaining a lower antibody concentration of $2\times10^{-2}$ ng/mL. The performance of each antibody was compared to a commercial clone (commercial mAb #2) (FIG. 10, left). The data shows that antibodies #A, #B and #D bind with higher signal-to-noise ratios (S/N) than the commercial antibody, mostly for concentrations between 20 and 2000 ng/mL, and these also display lower EC50 values when compared to the commercial mAb #2 (FIG. 10, right).

CONCLUSIONS

Functional assays have been performed where anti-HIV-1 antibodies #A, #B and #D have been compared with commercial anti-HIV-1 p24 antibodies from commercial mAbs #1 and #2. The binding affinities and potency of each antibody was evaluated by BLI and indirect ELISA. In both experiments, HIV-1 antibodies #A, #B and #D show better affinity and better EC50 values when compared to the commercial antibodies tested (FIG. 9 and Table 7 for kinetic analysis, and FIG. 10 for ELISA data).

The experimental data presented here demonstrate that the anti-HIV-1 antibodies of the present invention can be used to detect the HIV-1 structural p24 protein. Said antibodies show improved properties in terms of affinity, sensitivity, potency, expression, solubility and manufacturability when compared to similar products on the market and their use in serology can contribute to a reduction in the timeframe between the HIV-1 infection and diagnosis event; therefore, preventing secondary viral transmissions.

Concordance Table

| Name | Sequence | SEQ ID NO: |
|---|---|---|
| Light Chain mAb A | DIQMTQTTSSLSASLGDRVTINCRASQDISNYLHWYQQKPDG TVKLLIYYTSRLHSGVPSRFSGSGSGTDYSLTISNLEKEDIATY FCQQGNSFPWTFGGGTKVEIKRADAAPTVSIFPPSSEQLTSG GASVVCFLNNFYPKDINVKWKIDGSERQNGVLNSWTDQDSK DSTYSMSSTLTLTKDEYERHNSYTCEATHKTSTSPIVKSFNRN EC | 1 |
| Light Chain mAb B | DIVLTQSPATLSVTPGDSVSLSCRASQSISDNLHWYRQKSHE SPRLLIKYSSQSISGIPSRFSGSGSGTDFTLSINSVETEDFGMY FCQQSNSWPFTFGSGTNLELKRADAAPTVSIFPPSSEQLTSG GASVVCFLNNFYPKDINVKWKIDGSERQNGVLNSWTDQDSK DSTYSMSSTLTLTKDEYERHNSYTCEATHKTSTSPIVKSFNRN EC | 2 |
| Light Chain mAb D | DVVMTQTPLSLPVSLGDQASISCRSSQSLVNSDGNTFLQWLL QKPGQSPKLLIYKVSNRFSGVPDRFSGSGSGTDFTLRISRVEA EDLGVYFCSQSTHVPWTFGGGTKLEIKRADAAPTVSIFPPSSE QLTSGGASVVCFLNNFYPKDINVKWKIDGSERQNGVLNSWTD QDSKDSTYSMSSTLTLTKDEYERHNSYTCEATHKTSTSPIVKS FNRNEC | 3 |
| Heavy Chain mAb A | EVKLVESGGGLVKPGGSLQLSCVASGFTFSSYAMSWVRQTP EKGLEWVASITSGGNTYYPDSVKGRFTISRDNAGNILYLQMSS LRSEDTAMFYCAREVLSVPFAYWGQGTLVTVSTAKTTPPSVY PLAPGSAAQTNSMVTLGCLVKGYFPEPVTVTWNSGSLSSGV HTFPAVLQSDLYTLSSSVTVPSSTWPSETVTCNVAHPASSTK VDKKIVPRDCGCKPCICTVPEVSSVFIFPPKPKDVLTITLTPKVT CVVVDISKDDPEVQFSWFVDDVEVHTAQTQPREEQFNSTFR SVSELPIMHQDWLNGKEFKCRVNSAAFPAPIEKTISKTKGRPK APQVYTIPPPKEQMAKDKVSLTCMITDFFPEDITVEWQWNGQ PAENYKNTQPIMDTDGSYFVYSKLNVQKSNWEAGNTFTCSVL HEGLHNHHTEKSLSHSPG | 4 |
| Heavy Chain mAb B | EVOLVESGGGLVKPGGSLKLSCAASGFAFSSYDMSWVRQTP DKRLEWVAYITSGVGNLNYLDTVKGRFTISRDNAKNTLYLQM SSLRSEDTAMYFCLRPPSYFGSSYDAMDYWGRGTSVTVSSA KTTPPSVYPLAPGSAAQTNSMVTLGCLVKGYFPEPVTVTWNS GSLSSGVHTFPAVLQSDLYTLSSSVTVPSSTWPSETVTCNVA HPASSTKVDKKIVPRDCGCKPCICTVPEVSSVFIFPPKPKDVLT ITLTPKVTCVVVDISKDDPEVQFSWFVDDVEVHTAQTQPREE QFNSTFRSVSELPIMHQDWLNGKEFKCRVNSAAFPAPIEKTIS KTKGRPKAPQVYTIPPPKEQMAKDKVSLTCMITDFFPEDITVE WQWNGQPAENYKNTQPIMDTDGSYFVYSKLNVQKSNWEAG NTFTCSVLHEGLHNHHTEKSLSHSPG | 5 |
| Heavy Chain mAb D | QIQLQQSGPELVKPGASVKVSCKASGYAFTSYQLYWVKQSH GKSLEWIGYIDPYNGGTGYNQKFKGKATLTVDKSSSTAYMHL NSLTSEDSAVYYCASPRWLPAGDYWGQGTSVTVSSAKTTAP SVYPLAPVCGDTTGSSVTLGCLVKGYFPEPVTLTWNSGSLSS GVHTFPAVLQSDLYTLSSSVTVTSSTWPSQSITCNVAHPASST KVDKKIEPRGPTIKPCPPCKCPAPNLLGGPSVFIFPPKIKDVLMI SLTPKVTCVVVDVSEDDPDVQISWFVNNVEVHTAQTQTHRED YNSTLRVVSALPIQHQDWMSGKEFKCKVNNKDLPAPIERTISK PKGSVRAPQVYVLPPPEEEMTKKQVTLTCMVTDFMPEDIYVE WTNNGKTELNYKNTEPVLDSDGSYFMYSKLRVEKKNWVERN SYSCSVVHEGLHNHHTTKSFSRTPGK | 6 |
| VL Chain mAb A | DIQMTQTTSSLSASLGDRVTINCRASQDISNYLHWYQQKPDG TVKLLIYYTSRLHSGVPSRFSGSGSGTDYSLTISNLEKEDIATY FCQQGNSFPWTFGGGTKVEIK | 7 |
| VL Chain mAb B | DIVLTQSPATLSVTPGDSVSLSCRASQSISDNLHWYROKSHE SPRLLIKYSSQSISGIPSRFSGSGSGTDFTLSINSVETEDFGMY FCQQSNSWPFTFGSGTNLELK | 8 |
| VL Chain mAb D | DVVMTQTPLSLPVSLGDQASISCRSSQSLVNSDGNTFLQWLL QKPGQSPKLLIYKVSNRFSGVPDRFSGSGSGTDFTLRISRVEA EDLGVYFCSQSTHVPWTFGGGTKLEIK | 9 |

-continued

Concordance Table

| Name | Sequence | SEQ ID NO: |
|---|---|---|
| VH Chain mAb A | EVKLVESGGGLVKPGGSLQLSCVASGFTFSSYAMSWVRQTP EKGLEWVASITSGGNTYYPDSVKGRFTISRDNAGNILYLQMSS LRSEDTAMFYCAREVLSVPFAYWGQGTLVTVST | 10 |
| VH Chain mAb B | EVOLVESGGGLVKPGGSLKLSCAASGFAFSSYDMSWVRQTP DKRLEWVAYITSGVGNLNYLDTVKGRFTISRDNAKNTLYLQM SSLRSEDTAMYFCLRPPSYFGSSYDAMDYWGRGTSVTVSS | 11 |
| VH Chain mAb D | QIQLQQSGPELVKPGASVKVSCKASGYAFTSYQLYWVKQSH GKSLEWIGYIDPYNGGTGYNQKFKGKATLTVDKSSSTAYMHL NSLTSEDSAVYYCASPRWLPAGDYWGQGTSVTVSS | 12 |
| CL Chain mAbs A, B & D | RADAAPTVSIFPPSSEQLTSGGASVVCFLNNFYPKDINVKWKI DGSERQNGVLNSWTDQDSKDSTYSMSSTLTLTKDEYERHNS YTCEATHKTSTSPIVKSFNRNEC | 13 |
| CH Chain mAbs A & B | AKTTPPSVYPLAPGSAAQTNSMVTLGCLVKGYFPEPVTVTWN SGSLSSGVHTFPAVLQSDLYTLSSSVTVPSSTWPSETVTCNV AHPASSTKVDKKIVPRDCGCKPCICTVPEVSSVFIFPPKPKDVL TITLTPKVTCVVVDISKDDPEVQFSWFVDDVEVHTAQTQPREE QFNSTFRSVSELPIMHQDWLNGKEFKCRVNSAAFPAPIEKTIS KTKGRPKAPQVYTIPPPKEQMAKDKVSLTCMITDFFPEDITVE WQWNGQPAENYKNTQPIMDTDGSYFVYSKLNVQKSNWEAG NTFTCSVLHEGLHNHHTEKSLSHSPG | 14 |
| CDR 1 VL mAb A | RASQDISNYLH | 15 |
| CDR 2 VL mAb A | YTSRLHS | 16 |
| CDR 3 VL mAb A | QQGNSFPWT | 17 |
| CDR 1 VL mAb B | RASQSISDNLH | 18 |
| CDR 2 VL mAb B | YSSQSIS | 19 |
| CDR 3 VL mAb B | QQSNSWPFT | 20 |
| CDR 1 VL mAb D | RSSQSLVNSDGNTFLQ | 21 |
| CDR 2 VL mAb D | KVSNRFS | 22 |
| CDR 3 VL mAb D | SQSTHVPWT | 23 |
| CDR 1 VH mAb A | GFTFSSY | 24 |
| CDR 2 VH mAb A | TSGGN | 25 |
| CDR 3 VH mAb A | EVLSVPFAY | 26 |
| CDR 1 VH mAb B | GFAFSSY | 27 |
| CDR 2 VH mAb B | TSGVGN | 28 |
| CDR 3 VH mAb B | PPSYFGSSYDAMDY | 29 |
| CDR 1 VH mAb D | GYAFTSY | 30 |

-continued

Concordance Table

| Name | Sequence | SEQ ID NO: |
|---|---|---|
| CDR 2 VH mAb D | DPYNGG | 31 |
| CDR 3 VH mAb D | PRWLPAGDY | 32 |
| Epitope mAb D | PIAPGQM | 33 |
| CH Chain mAb D | AKTTAPSVYPLAPVCGDTTGSSVTLGCLVKGYFPEPVTLTWN<br>SGSLSSGVHTFPAVLQSDLYTLSSSVTVTSSTWPSQSITCNVA<br>HPASSTKVDKKIEPRGPTIKPCPPCKCPAPNLLGGPSVFIFPPK<br>IKDVLMISLTPKVTCVVVDVSEDDPDVQISWFVNNVEVHTAQT<br>QTHREDYNSTLRVVSALPIQHQDWMSGKEFKCKVNNKDLPA<br>PIERTISKPKGSVRAPQVYVLPPPEEEMTKKQVTLTCMVTDFM<br>PEDIYVEWTNNGKTELNYKNTEPVLDSDGSYFMYSKLRVEKK<br>NWVERNSYSCSVVHEGLHNHHTTKSFSRTPGK | 34 |
| P24 Antigen Variant 1 | ALDKIEEEQNKSKKKAQXAAAADAGNSSQVSQNYPIVQNLQG<br>QMVHQAISPRTLNAWVKVVEEKAFSPEVIPMFSALSEGATPQ<br>DLNTMLNTVGGHQAAMQMLKETINEEAAEWDRLHPVHAGPIA<br>PGQMREPRGSDIAGTTSTLQEQIGWMTNNPPIPVGEIYKRWII<br>LGLNKIVRMYSPTSILDIRQGPKEPFRDYVDRFYKTLRAEQAS<br>QEVKNWMTETLLVQNANPDCKTILKALGPAATLEEMMTACQG<br>VGGPGHKARVLAEAMSQVTNNSATI | 35 |
| P24 Antigen Variant 2 | MPIVQNLQGQMVHQAISPRTLNAWVKVVEEKAFSPEVIPMFS<br>ALSEGATPQDLNTMLNTVGGHQAAMQMLKETINEEAAEWRD<br>VHPVHAGPIAPGQMREPRGSDIAGTTSTLQEQIGWMTNNPPI<br>PVGEIYKRWIILGLNKIVRMYSPTSILDIRQGPKEPFRDYVDRF<br>YKTLRAEQASQDVKNWMTETLLVQNANPDCKTILKALGPAAT<br>LEEMMTACQGVGGPGHKARVL | 36 |
| Nucleotide sequence for VL mAb A | ATGGAGACCGACACCCTGCTGCTCTGGGTGCTGCTGCTCT<br>GGGTGCCCGGCTCCACCGGAGACATCCAGATGACCCAGA<br>CCACCAGCTCCCTGAGCGCCAGCCTGGGCGACAGGGTGA<br>CCATCAACTGCAGGGCCAGCCAGGACATCAGCAACTACCT<br>GCACTGGTATCAACAGAAGCCCGACGGCACGGTGAAACTG<br>CTGATCTACTATACCAGCAGGCTGCACAGCGGCGTGCCCA<br>GCCGCTTCTCCGGTAGCGGCAGCGGCACCGACTACTCTCT<br>GACCATTAGCAACCTGGAGAAGGAGGACATTGCCACCTAC<br>TTCTGTCAGCAGGGCAACAGCTTCCCCTGGACCTTCGGCG<br>GAGGAACCAAAGTGGAAATCAAGCGGGCAGATGCTGCACC<br>AACTGTATCCATCTTCCCACCATCCAGTGAGCAGTTAACAT<br>CTGGAGGTGCCTCAGTCGTGTGCTTCTTGAACAACTTCTAC<br>CCCAAAGACATCAATGTCAAGTGGAAGATTGATGGCAGTG<br>AACGACAAAATGGCGTCCTGAACAGTTGGACTGATCAGGA<br>CAGCAAAGACAGCACCTACAGCATGAGCAGCACCCTCACG<br>TTGACCAAGGACGAGTATGAACGACATAACAGCTATACCTG<br>TGAGGCCACTCACAAGACATCAACTTCACCCATTGTCAAGA<br>GCTTCAACAGGAATGAGTGTTGA | 37 |
| Nucleotide sequence for VH mAb A | ATGGACCCCAAGGGCAGCCTGAGCTGGAGAATCCTGCTGT<br>TCCTGAGCCTGGCCTTCGAGCTGAGCTACGGCGAGGTGAA<br>GCTCGTGGAGAGCGGCGGTGGCCTGGTTAAGCCTGGGGG<br>AAGCCTGCAGCTGAGCTGCGTGGCCAGCGGCTTCACGTTC<br>AGCAGCTACGCCATGAGCTGGGTGAGGCAGACCCCCGAG<br>AAGGGCCTGGAGTGGGTGGCAAGCATCACCAGCGGGGGT<br>AACACCTACTACCCCGACAGCGTGAAGGGCAGGTTCACCA<br>TCAGCAGGGACAACGCTGGCAACATCCTGTACCTGCAGAT<br>GAGCAGCCTGAGGAGCGAGGACACCGCCATGTTCTACTGC<br>GCCAGGGAGGTGCTGAGCGTCCCCTTCGCCTACTGGGGC<br>CAGGGCACCCTGGTCACAGTGAGCACCGCCAAGACCACTC<br>CACCTTCCGTGTACCCTCTGGCTCCTGGATCTGCCGCCCA<br>GACCAACTCCATGGTCACCCTGGGCTGCCTCGTGAAGGGC<br>TACTTCCCTGAGCCTGTGACCGTGACCTGGAACTCCGGCT<br>CTCTGTCCTCTGGCGTGCACACCTTCCCTGCCGTGCTGCA<br>GTCCGACCTGTACACCCTGTCCTCCAGCGTGACCGTGCCT<br>TCCTCTACCTGGCCCTCCGAGACAGTGACCTGCAACGTGG<br>CCCACCCTGCCAGCTCTACCAAGGTGGACAAGAAAATCGT<br>GCCCCGGGACTGCGGCTGCAAGCCCTGTATCTGTACCGTG<br>CCCGAGGTGTCCTCCGTGTTCATCTTCCCACCCAAGCCCA<br>AGGACGTGCTGACCATCACCCTGACCCCCAAAGTGACCTG<br>TGTGGTGGTGGACATCTCCAAGGACGACCCCGAGGTGCA | 38 |

-continued

Concordance Table

| Name | Sequence | SEQ ID NO: |
|---|---|---|
| | GTTCAGTTGGTTCGTGGACGACGTGGAAGTGCACACCGCT<br>CAGACCCAGCCCAGAGAGGAACAGTTCAACTCCACCTTCA<br>GATCCGTGTCCGAGCTGCCCATCATGCACCAGGACTGGCT<br>GAACGGCAAAGAGTTCAAGTGCAGAGTGAACTCCGCCGCC<br>TTCCCAGCCCCCATCGAAAAGACCATCAGCAAGACCAAGG<br>GCAGACCCAAGGCCCCCCAGGTGTACACAATCCCGCCACC<br>CAAAGAACAGATGGCCAAGGACAAGGTGTCCCTGACCTGC<br>ATGATCACCGATTTCTTCCCAGAGGATATTACCGTGGAATG<br>GCAGTGGAACGGCCAGCCCGCCGAGAACTACAAGAACAC<br>CCAGCCTATCATGGACACCGACGGCTCCTACTTCGTGTAC<br>TCCAAGCTGAACGTGCAGAAGTCCAACTGGGAGGCCGGCA<br>ACACCTTCACCTGTAGCGTGCTGCACGAGGGCCTGCACAA<br>TCACCACACCGAGAAGTCCCTGTCCCACTCCCCTGGCTAG | |
| Nucleotide sequence for VL mAb B | ATGGAGACCGACACCCTGCTGCTCTGGGTGCTGCTGCTCT<br>GGGTGCCCGGCTCCACCGGAGACATCGTGCTGACCCAGA<br>GCCCTGCCACCCTGAGCGTGACCCCTGGCGACAGCGTGA<br>GCCTGAGCTGCAGGGCCAGCCAGAGCATTAGCGACAACCT<br>GCACTGGTACAGGCAGAAAAGCCACGAAAGCCCCAGGCTT<br>CTGATCAAGTACAGCAGCCAAAGCATCTCAGGCATCCCCA<br>GCAGGTTCAGTGGGAGCGGCAGCGGCACCGACTTCACCC<br>TGTCCATCAACAGCGTTGAGACCGAGGACTTCGGCATGTA<br>CTTCTGCCAGCAGAGCAACAGCTGGCCGTTTACCTTCGGC<br>TCCGGCACTAACCTGGAGCTGAAGCGGGCAGATGCTGCAC<br>CAACTGTATCCATCTTCCCACCATCCAGTGAGCAGTTAACA<br>TCTGGAGGTGCCTCAGTCGTGTGCTTCTTGAACAACTTCTA<br>CCCCAAAGACATCAATGTCAAGTGGAAGATTGATGGCAGT<br>GAACGACAAAATGGCGTCCTGAACAGTTGGACTGATCAGG<br>ACAGCAAAGACAGCACCTACAGCATGAGCAGCACCCTCAC<br>GTTGACCAAGGACGAGTATGAACGACATAACAGCTATACCT<br>GTGAGGCCACTCACAAGACATCAACTTCACCCATTGTCAAG<br>AGCTTCAACAGGAATGAGTGTTGA | 39 |
| Nucleotide sequence for VH mAb B | ATGGACCCCAAGGGCAGCCTGAGCTGGAGAATCCTGCTGT<br>TCCTGAGCCTGGCCTTCGAGCTGAGCTACGGCGAGGTGCA<br>GCTGGTGGAGAGCGGGGGTGGACTTGTGAAGCCCGGTGG<br>CTCACTGAAGCTGAGCTGCGCGGCAAGCGGCTTCGCCTTC<br>AGCAGCTACGACATGAGCTGGGTGAGGCAGACCCCCGAC<br>AAGAGGCTGGAGTGGGTGGCCTACATCACCAGTGGCGTG<br>GGCAACCTGAACTACCTGGACACCGTGAAGGGCAGGTTCA<br>CCATCAGCAGGGACAACGCCAAGAACACCCTGTACCTGCA<br>GATGAGCAGCTTGAGGAGCGAAGACACCGCCATGTACTTC<br>TGCCTGAGACCGCCCAGCTACTTCGGCTCTAGCTATGATG<br>CCATGGACTACTGGGGCAGGGGTACTAGCGTGACCGTGA<br>GCTCTGCCAAGACCACTCCACCTTCCGTGTACCCTCTGGC<br>TCCTGGATCTGCCGCCCAGACCAACTCCATGGTCACCCTG<br>GGCTGCCTCGTGAAGGGCTACTTCCCTGAGCCTGTGACCG<br>TGACCTGGAACTCCGGCTCTCTGTCCTCTGGCGTGCACAC<br>CTTCCCTGCCGTGCTGCAGTCCGACCTGTACACCCTGTCC<br>TCCAGCGTGACCGTGCCTTCCTCTACCTGGCCCTCCGAGA<br>CAGTGACCTGCAACGTGGCCCACCCTGCCAGCTCTACCAA<br>GGTGGACAAGAAAATCGTGCCCCGGGACTGCGGCTGCAA<br>GCCCTGTATCTGTACCGTGCCCGAGGTGTCCTCCGTGTTC<br>ATCTTCCCACCCAAGCCCAAGGACGTGCTGACCATCACCC<br>TGACCCCCAAAGTGACCTGTGTGGTGGTGGACATCTCCAA<br>GGACGACCCCGAGGTGCAGTTCAGTTGGTTCGTGGACGAC<br>GTGGAAGTGCACACCGCTCAGACCCAGCCCAGAGAGGAA<br>CAGTTCAACTCCACCTTCAGATCCGTGTCCGAGCTGCCCAT<br>CATGCACCAGGACTGGCTGAACGGCAAAGAGTTCAAGTGC<br>AGAGTGAACTCCGCCGCCTTCCCAGCCCCCATCGAAAAGA<br>CCATCAGCAAGACCAAGGGCAGACCCAAGGCCCCCCAGG<br>TGTACACAATCCCGCCACCCAAAGAACAGATGGCCAAGGA<br>CAAGGTGTCCCTGACCTGCATGATCACCGATTTCTTCCCAG<br>AGGATATTACCGTGGAATGGCAGTGGAACGGCCAGCCCGC<br>CGAGAACTACAAGAACACCCAGCCTATCATGGACACCGAC<br>GGCTCCTACTTCGTGTACTCCAAGCTGAACGTGCAGAAGT<br>CCAACTGGGAGGCCGGCAACACCTTCACCTGTAGCGTGCT<br>GCACGAGGGCCTGCACAATCACCACACCGAGAAGTCCCTG<br>TCCCACTCCCCTGGCTAG | 40 |

-continued

Concordance Table

| Name | Sequence | SEQ ID NO: |
|---|---|---|
| Nucleotide sequence for VL mAb D | ATGGAGACCGACACCCTGCTGCTCTGGGTGCTGCTGCTCT<br>GGGTGCCCGGCTCCACCGGAGACGTGGTGATGACCCAGA<br>CACCCCTGAGTCTGCCCGTGAGCTTGGGCGACCAGGCCA<br>GCATCAGCTGTAGGAGCTCACAGAGCCTGGTGAACAGCGA<br>CGGCAACACCTTCCTGCAGTGGCTCCTGCAAAAACCCGGC<br>CAAAGCCCGAAGCTGCTTATATACAAGGTGAGCAATAGGTT<br>CAGTGGTGTGCCCGACCGCTTCAGCGGCAGCGGTAGCGG<br>CACCGACTTCACCCTGAGGATCAGCAGGGTGGAGGCCGA<br>GGACCTGGGCGTGTACTTCTGCAGCCAGAGCACCCACGTG<br>CCCTGGACCTTCGGCGGAGGAACCAAACTGGAAATCAAGC<br>GGGCAGATGCTGCACCAACTGTATCCATCTTCCCACCATC<br>CAGTGAGCAGTTAACATCTGGAGGTGCCTCAGTCGTGTGC<br>TTCTTGAACAACTTCTACCCCAAAGACATCAATGTCAAGTG<br>GAAGATTGATGGCAGTGAACGACAAAATGGCGTCCTGAAC<br>AGTTGGACTGATCAGGACAGCAAAGACAGCACCTACAGCA<br>TGAGCAGCACCCTCACGTTGACCAAGGACGAGTATGAACG<br>ACATAACAGCTATACCTGTGAGGCCACTCACAAGACATCAA<br>CTTCACCCATTGTCAAGAGCTTCAACAGGAATGAGTGTTGA | 41 |
| Nucleotide sequence for VH mAb D | ATGGAGACCGACACCCTGCTGCTCTGGGTGCTGCTGCTCT<br>GGGTGCCCGGCTCCACCGGACAGATCCAGCTGCAACAAA<br>GCGGCCCTGAGCTGGTGAAGCCCGGTGCTAGCGTGAAGG<br>TGAGCTGTAAGGCAAGCGGCTACGCCTTCACAAGTTACCA<br>GCTGTACTGGGTAAAGCAAAGCCACGGCAAGAGCCTGGAG<br>TGGATCGGCTATATCGACCCCTACAACGGCGGCACCGGCT<br>ACAACCAGAAGTTCAAGGGTAAGGCCACCTTGACCGTGGA<br>CAAGAGCAGCAGCACCGCCTACATGCATCTGAACAGCCTG<br>ACCAGCGAGGACAGCGCCGTGTACTACTGCGCCAGCCCC<br>AGGTGGCTTCCCGCTGGCGACTACTGGGGCCAGGGCACC<br>AGCGTGACTGTGAGCTCTGCTAAAACAACAGCCCCATCGG<br>TCTATCCACTGGCCCCTGTGTGTGGAGATACAACTGGCTC<br>CTCGGTGACTCTAGGATGCCTGGTCAAGGGTTATTTCCCT<br>GAGCCAGTGACCTTGACCTGGAACTCTGGTTCCCTGTCCA<br>GTGGTGTGCACACCTTCCCAGCTGTCCTGCAGTCTGACCT<br>CTACACCCTCAGCTCAAGCGTGACTGTAACCAGCTCGACC<br>TGGCCCAGCCAGTCCATCACCTGCAATGTGGCCCACCCGG<br>CAAGCAGCACCAAGGTGGACAAGAAAATTGAGCCCAGAGG<br>GCCCACAATCAAGCCCTGTCCTCCATGCAAATGCCCAGCA<br>CCTAACCTCTTGGGTGGACCATCCGTCTTCATCTTCCCTCC<br>AAAGATCAAGGATGTACTCATGATCTCCCTGAGCCCCATAG<br>TCACATGTGTAGTCGTTGATGTGAGCGAGGATGACCCAGA<br>TGTCCAGATCAGCTGGTTTGTGAACAACGTGGAAGTGCAC<br>ACTGCTCAGACACAGACGCATAGAGAGGATTACAACAGTA<br>CTCTCCGGGTTGTCAGTGCCCTCCCCATCCAGCACCAGGA<br>CTGGATGAGTGGCAAGGAGTTCAAATGCAAGGTCAACAAC<br>AAAGACCTCCCAGCGCCCATCGAGAGAACCATCTCAAAAC<br>CCAAAGGGTCAGTAAGAGCTCCACAGGTATATGTCTTGCCT<br>CCACCAGAAGAGGAGATGACTAAGAAACAGGTCACTCTGA<br>CCTGCATGGTCACAGACTTCATGCCTGAAGACATTTACGTG<br>GAGTGGACCAACAACGGGAAAACAGAGCTAAACTACAAGA<br>ACACTGAACCAGTCCTGGACTCTGATGGTTCTTACTTCATG<br>TACAGCAAGCTGAGAGTGGAGAAGAAGAACTGGGTGGAGA<br>GAAATAGCTACTCCTGTTCAGTGGTCCACGAGGGTCTGCA<br>CAATCACCACACGACTAAGAGCTTCTCCCGGACTCCGGGT<br>TAG | 42 |

*Unless otherwise stated all CDR sequences have been derived according to Chothia utilizing the Abysis database.

The invention claimed is:

1. An anti-HIV-1 antibody or fragment thereof comprising a light chain comprising complementary determining regions L-CDR1, L-CDR2 and L-CDR3 and a heavy chain comprising complementary determining regions H-CDR1, H-CDR2 and H-CDR3, wherein the L-CDR1, L-CDR2, L-CDR3, H-CDR1, H-CDR2 and H-CDR3 are selected from the group consisting of (a), (b), and (c) below:

(a) the amino acid sequence of L-CDR1 comprises SEQ ID NO: 18,
 the amino acid sequence of L-CDR2 comprises SEQ ID NO: 19,
 the amino acid sequence of L-CDR3 comprises SEQ ID NO: 20,
 the amino acid sequence of H-CDR1 comprises SEQ ID NO: 27,
 the amino acid sequence of H-CDR2 comprises SEQ ID NO: 28,
 the amino acid sequence of H-CDR3 comprises SEQ ID NO: 29, (b) the amino acid sequence of L-CDR1 comprises SEQ ID NO: 15,
 the amino acid sequence of L-CDR2 comprises SEQ ID NO: 16,
 the amino acid sequence of L-CDR3 comprises SEQ ID NO: 17,
 the amino acid sequence of H-CDR1 comprises SEQ ID NO: 24,
 the amino acid sequence of H-CDR2 comprises SEQ ID NO: 25,
 the amino acid sequence of H-CDR3 comprises SEQ ID NO: 26, (c) the amino acid sequence of L-CDR1 comprises SEQ ID NO: 21,
 the amino acid sequence of L-CDR2 comprises SEQ ID NO: 22,
 the amino acid sequence of L-CDR3 comprises SEQ ID NO: 23,
 the amino acid sequence of H-CDR1 comprises SEQ ID NO: 30,
 the amino acid sequence of H-CDR2 comprises SEQ ID NO: 31,
 the amino acid sequence of H-CDR3 comprises SEQ ID NO: 32.

2. The anti-HIV-1 antibody of claim 1, wherein:

(i) when the anti-HIV-1 antibody is the antibody of (a), the variable region of the light chain comprises a sequence having about 90% homology with an amino acid sequence SEQ ID NO: 8;

(ii) when the anti-HIV-1 antibody is the antibody of (b), the variable region of the light chain comprises a sequence having about 90% homology with an amino acid sequence SEQ ID NO: 7;

(iii) when the anti-HIV-1 antibody is the antibody of (c), the variable region of the light chain comprises a sequence having about 90% homology with an amino acid sequence SEQ ID NO: 9.

3. The anti-HIV-1 antibody of claim 2, wherein:

(i) when the anti-HIV-1 antibody is the antibody of (i) of claim 2, the variable region of the heavy chain comprises a sequence having about 90% homology with the amino acid sequence SEQ ID NO: 11;

(ii) when the anti-HIV-1 antibody is the antibody of (ii) of claim 2, the variable region of the heavy chain comprises a sequence having about 90% homology with the amino acid sequence SEQ ID NO: 10;

(iii) when the anti-HIV-1 antibody is the antibody of (iii) of claim 2, the variable region of the heavy chain comprises a sequence having about 90% homology with the amino acid sequence SEQ ID NO: 12.

4. The anti-HIV-1 antibody of claim 3, wherein:

(i) when the anti-HIV-1 antibody is the antibody of (i) of claim 3, the light chain of said antibody comprises the amino acid sequence SEQ ID NO: 2;

(ii) when the anti-HIV-1 antibody is the antibody of (ii) of claim 3, the light chain of said antibody comprises the amino acid sequence SEQ ID NO: 1;

(iii) when the anti-HIV-1 antibody is the antibody of (iii) of claim 3, the light chain of said antibody comprises the amino acid sequence SEQ ID NO: 3.

5. The anti-HIV-1 antibody of claim 4, wherein:

(i) when the anti-HIV-1 antibody is the antibody of (i) of claim 4, the heavy chain of said antibody comprises the amino acid sequence SEQ ID NO: 5;

(ii) when the anti-HIV-1 antibody is the antibody of (ii) of claim 4, the heavy chain of said antibody comprises the amino acid sequence SEQ ID NO: 4;

(iii) when the anti-HIV-1 antibody is the antibody of (iii) of claim 4, the heavy chain of said antibody comprises the amino acid sequence SEQ ID NO: 6.

6. The anti-HIV-1 antibody of claim 1, wherein the antibody is a monoclonal antibody or a recombinant antibody, or a fragment thereof.

7. The anti-HIV-1 antibody of claim 1, wherein said antibody is an antibody fragment, wherein the antibody fragment is selected from variable fragments (Fv), single-chain Fvs (scFv), bispecific antibodies (sc(Fv)2), single chain antibodies, single domain antibodies, Fab fragments, F(ab')2 fragments, Fab' fragments, disulfide-linked Fv (dsFv), chemically conjugated Fv (ccFv), diabodies, anti-idiotypic (anti-Id) antibodies, affibodies, nanobodies, and unibodies.

8. The anti-HIV-1 antibody of claim 1, wherein the antibody comprises a constant region of the murine IgG1 class or the murine IgG2a class.

9. The anti-HIV-1 antibody of claim 8, wherein the antibody is bound to a solid support.

10. The anti-HIV-1 antibody of claim 1, wherein (i) when the anti-HIV-1 antibody is the antibody of (a), the variable region of the light chain comprises the amino acid sequence SEQ ID NO: 8;

(ii) when the anti-HIV-1 antibody is the antibody of (b), the variable region of the light chain comprises the amino acid sequence SEQ ID NO: 7;

(iii) when the anti-HIV-1 antibody is the antibody of (c), the variable region of the light chain comprises the amino acid sequence SEQ ID NO: 9.

11. The anti-HIV-1 antibody of claim 10, wherein (i) when the anti-HIV-1 antibody is the antibody of (i) of claim 10, the variable region of the heavy chain comprises the amino acid sequence SEQ ID NO: 11;

(ii) when the anti-HIV-1 antibody is the antibody of (ii) of claim 10, the variable region of the heavy chain comprises the amino acid sequence SEQ ID NO: 10;

(iii) when the anti-HIV-1 antibody is the antibody of (iii) of claim 10, the variable region of the heavy chain comprises the amino acid sequence SEQ ID NO: 12.

12. A composition comprising the anti-HIV-1 antibody of claim 5 and a solid support, wherein the anti-HIV-1 antibody is covalently or non-covalently bound to the solid support.

13. A kit for detecting the presence of HIV-1 in a sample, the kit comprising at least one anti-HIV-1 antibody, wherein the at least one antibody is one of (i)-(iii) of claim 5 and a solid support, wherein said at least one antibody is covalently or non-covalently bound to the solid support.

14. A composition comprising the anti-HIV-1 antibody of claim 1 and a solid support.

15. The composition of claim 14, wherein the solid support comprises a particle, a bead, a membrane, a surface, a polypeptide chip, a microtiter plate, or the solid-phase of a chromatography column.

16. The composition of claim 14, wherein the anti-HIV-1 antibody is covalently or non-covalently bound to the solid support.

17. A kit for detecting the presence of HIV-1 in a sample, the kit comprising at least one anti-HIV-1 antibody, wherein the at least one anti-HIV-1 antibody is at least one of (a)-(c) of claim 1 and a solid support.

18. The kit of claim 17, wherein said at least one antibody is covalently or non-covalently bound to the solid support.

19. A nucleic acid comprising a nucleotide sequence encoding the anti-HIV-1 antibody of claim 1, a promoter operably linked to the nucleotide sequence and a selectable marker.

20. An anti-HIV-1 antibody, which specifically binds to an epitope of HIV-1 p24 protein consisting of an amino acid sequence of SEQ ID NO: 33, wherein the anti-HIV-1 antibody comprises a light chain comprising complementary determining regions L-CDR1, L-CDR2 and L-CDR3 and a heavy chain comprising complementary determining regions H-CDR1, H-CDR2 and H-CDR3, wherein the amino acid sequence of L-CDR1 comprises SEQ ID NO: 21, the amino acid sequence of L-CDR2 comprises SEQ ID NO: 22, the amino acid sequence of L-CDR3 comprises SEQ ID NO: 23, the amino acid sequence of H-CDR1 comprises SEQ ID NO: 30, the amino acid sequence of H-CDR2 comprises SEQ ID NO: 31, the amino acid sequence of H-CDR3 comprises SEQ ID NO: 32.

* * * * *

SEQUENCE LISTING

<160> NUMBER OF SEQ ID NOS: 42

<210> SEQ ID NO 1
<211> LENGTH: 214
<212> TYPE: PRT
<213> ORGANISM: Artificial Sequence
<220> FEATURE:
<223> OTHER INFORMATION: Light chain mAb A

<400> SEQUENCE: 1

```
Asp Ile Gln Met Thr Gln Thr Thr Ser Ser Leu Ser Ala Ser Leu Gly
1               5                   10                  15

Asp Arg Val Thr Ile Asn Cys Arg Ala Ser Gln Asp Ile Ser Asn Tyr
            20                  25                  30

Leu His Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Lys
65                  70                  75                  80

Glu Asp Ile Ala Thr Tyr Phe Cys Gln Gln Gly Asn Ser Phe Pro Trp
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 2
<211> LENGTH: 214
<212> TYPE: PRT
<213> ORGANISM: Artificial Sequence
<220> FEATURE:
<223> OTHER INFORMATION: Light chain mAb B

<400> SEQUENCE: 2

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asp Asn
            20                  25                  30

Leu His Trp Tyr Arg Gln Lys Ser His Glu Ser Pro Arg Leu Leu Ile
        35                  40                  45

Lys Tyr Ser Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Phe
                85                  90                  95

Thr Phe Gly Ser Gly Thr Asn Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140
```

```
Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 3
<211> LENGTH: 219
<212> TYPE: PRT
<213> ORGANISM: Artificial Sequence
<220> FEATURE:
<223> OTHER INFORMATION: Light chain mAb D

<400> SEQUENCE: 3

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Asn Ser
            20                  25                  30

Asp Gly Asn Thr Phe Leu Gln Trp Leu Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215


<210> SEQ ID NO 4
<211> LENGTH: 440
<212> TYPE: PRT
<213> ORGANISM: Artificial Sequence
<220> FEATURE:
<223> OTHER INFORMATION: Heavy chain mAb A

<400> SEQUENCE: 4

Glu Val Lys Leu Val Glu Ser Gly Gly Gly Leu Val Lys Pro Gly Gly
```

-continued

```
1               5                   10                  15

Ser Leu Gln Leu Ser Cys Val Ala Ser Gly Phe Thr Phe Ser Ser Tyr
            20                  25                  30

Ala Met Ser Trp Val Arg Gln Thr Pro Glu Lys Gly Leu Glu Trp Val
        35                  40                  45

Ala Ser Ile Thr Ser Gly Gly Asn Thr Tyr Tyr Pro Asp Ser Val Lys
    50                  55                  60

Gly Arg Phe Thr Ile Ser Arg Asp Asn Ala Gly Asn Ile Leu Tyr Leu
65                  70                  75                  80

Gln Met Ser Ser Leu Arg Ser Glu Asp Thr Ala Met Phe Tyr Cys Ala
                85                  90                  95

Arg Glu Val Leu Ser Val Pro Phe Ala Tyr Trp Gly Gln Gly Thr Leu
            100                 105                 110

Val Thr Val Ser Thr Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430
```

```
Lys Ser Leu Ser His Ser Pro Gly
        435                 440


<210> SEQ ID NO 5
<211> LENGTH: 446
<212> TYPE: PRT
<213> ORGANISM: Artificial Sequence
<220> FEATURE:
<223> OTHER INFORMATION: Heavy chain mAb B

<400> SEQUENCE: 5

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Asp Lys Arg Leu Glu Trp Val
        35                  40                  45

Ala Tyr Ile Thr Ser Gly Val Gly Asn Leu Asn Tyr Leu Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Phe Cys
                85                  90                  95

Leu Arg Pro Pro Ser Tyr Phe Gly Ser Ser Tyr Asp Ala Met Asp Tyr
            100                 105                 110

Trp Gly Arg Gly Thr Ser Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350
```

Pro Pro Lys Glu Gln Met Ala Lys Asp Lys Val Ser Leu Thr Cys Met
355 360 365

Ile Thr Asp Phe Phe Pro Glu Asp Ile Thr Val Glu Trp Gln Trp Asn
370 375 380

Gly Gln Pro Ala Glu Asn Tyr Lys Asn Thr Gln Pro Ile Met Asp Thr
385 390 395 400

Asp Gly Ser Tyr Phe Val Tyr Ser Lys Leu Asn Val Gln Lys Ser Asn
405 410 415

Trp Glu Ala Gly Asn Thr Phe Thr Cys Ser Val Leu His Glu Gly Leu
420 425 430

His Asn His His Thr Glu Lys Ser Leu Ser His Ser Pro Gly
435 440 445

<210> SEQ ID NO 6
<211> LENGTH: 448
<212> TYPE: PRT
<213> ORGANISM: Artificial Sequence
<220> FEATURE:
<223> OTHER INFORMATION: Heavy chain mAb D

<400> SEQUENCE: 6

Gln Ile Gln Leu Gln Gln Ser Gly Pro Glu Leu Val Lys Pro Gly Ala
1 5 10 15

Ser Val Lys Val Ser Cys Lys Ala Ser Gly Tyr Ala Phe Thr Ser Tyr
20 25 30

Gln Leu Tyr Trp Val Lys Gln Ser His Gly Lys Ser Leu Glu Trp Ile
35 40 45

Gly Tyr Ile Asp Pro Tyr Asn Gly Gly Thr Gly Tyr Asn Gln Lys Phe
50 55 60

Lys Gly Lys Ala Thr Leu Thr Val Asp Lys Ser Ser Ser Thr Ala Tyr
65 70 75 80

Met His Leu Asn Ser Leu Thr Ser Glu Asp Ser Ala Val Tyr Tyr Cys
85 90 95

Ala Ser Pro Arg Trp Leu Pro Ala Gly Asp Tyr Trp Gly Gln Gly Thr
100 105 110

Ser Val Thr Val Ser Ser Ala Lys Thr Thr Ala Pro Ser Val Tyr Pro
115 120 125

Leu Ala Pro Val Cys Gly Asp Thr Thr Gly Ser Ser Val Thr Leu Gly
130 135 140

Cys Leu Val Lys Gly Tyr Phe Pro Glu Pro Val Thr Leu Thr Trp Asn
145 150 155 160

Ser Gly Ser Leu Ser Ser Gly Val His Thr Phe Pro Ala Val Leu Gln
165 170 175

Ser Asp Leu Tyr Thr Leu Ser Ser Ser Val Thr Val Thr Ser Ser Thr
180 185 190

Trp Pro Ser Gln Ser Ile Thr Cys Asn Val Ala His Pro Ala Ser Ser
195 200 205

Thr Lys Val Asp Lys Lys Ile Glu Pro Arg Gly Pro Thr Ile Lys Pro
210 215 220

Cys Pro Pro Cys Lys Cys Pro Ala Pro Asn Leu Leu Gly Gly Pro Ser
225 230 235 240

Val Phe Ile Phe Pro Pro Lys Ile Lys Asp Val Leu Met Ile Ser Leu
245 250 255

Thr Pro Lys Val Thr Cys Val Val Val Asp Val Ser Glu Asp Asp Pro
260 265 270

Asp Val Gln Ile Ser Trp Phe Val Asn Asn Val Glu Val His Thr Ala
275 280 285

Gln Thr Gln Thr His Arg Glu Asp Tyr Asn Ser Thr Leu Arg Val Val
290 295 300

Ser Ala Leu Pro Ile Gln His Gln Asp Trp Met Ser Gly Lys Glu Phe
305 310 315 320

Lys Cys Lys Val Asn Asn Lys Asp Leu Pro Ala Pro Ile Glu Arg Thr
325 330 335

Ile Ser Lys Pro Lys Gly Ser Val Arg Ala Pro Gln Val Tyr Val Leu
340 345 350

Pro Pro Pro Glu Glu Glu Met Thr Lys Lys Gln Val Thr Leu Thr Cys
355 360 365

Met Val Thr Asp Phe Met Pro Glu Asp Ile Tyr Val Glu Trp Thr Asn
370 375 380

Asn Gly Lys Thr Glu Leu Asn Tyr Lys Asn Thr Glu Pro Val Leu Asp
385 390 395 400

Ser Asp Gly Ser Tyr Phe Met Tyr Ser Lys Leu Arg Val Glu Lys Lys
405 410 415

Asn Trp Val Glu Arg Asn Ser Tyr Ser Cys Ser Val Val His Glu Gly
420 425 430

Leu His Asn His His Thr Thr Lys Ser Phe Ser Arg Thr Pro Gly Lys
435 440 445

<210> SEQ ID NO 7
<211> LENGTH: 107
<212> TYPE: PRT
<213> ORGANISM: Artificial Sequence
<220> FEATURE:
<223> OTHER INFORMATION: VL chain mAb A

<400> SEQUENCE: 7

Asp Ile Gln Met Thr Gln Thr Thr Ser Ser Leu Ser Ala Ser Leu Gly
1 5 10 15

Asp Arg Val Thr Ile Asn Cys Arg Ala Ser Gln Asp Ile Ser Asn Tyr
20 25 30

Leu His Trp Tyr Gln Gln Lys Pro Asp Gly Thr Val Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Lys
65 70 75 80

Glu Asp Ile Ala Thr Tyr Phe Cys Gln Gln Gly Asn Ser Phe Pro Trp
85 90 95

Thr Phe Gly Gly Gly Thr Lys Val Glu Ile Lys
100 105

<210> SEQ ID NO 8
<211> LENGTH: 107
<212> TYPE: PRT
<213> ORGANISM: Artificial Sequence
<220> FEATURE:
<223> OTHER INFORMATION: VL chain mAb B

<400> SEQUENCE: 8

Asp Ile Val Leu Thr Gln Ser Pro Ala Thr Leu Ser Val Thr Pro Gly
1 5 10 15

Asp Ser Val Ser Leu Ser Cys Arg Ala Ser Gln Ser Ile Ser Asp Asn

```
            20                  25                  30

Leu His Trp Tyr Arg Gln Lys Ser His Glu Ser Pro Arg Leu Leu Ile
        35                  40                  45

Lys Tyr Ser Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Phe
                85                  90                  95

Thr Phe Gly Ser Gly Thr Asn Leu Glu Leu Lys
            100                 105


<210> SEQ ID NO 9
<211> LENGTH: 112
<212> TYPE: PRT
<213> ORGANISM: Artificial Sequence
<220> FEATURE:
<223> OTHER INFORMATION: VL chain mAb D

<400> SEQUENCE: 9

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Asn Ser
            20                  25                  30

Asp Gly Asn Thr Phe Leu Gln Trp Leu Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110


<210> SEQ ID NO 10
<211> LENGTH: 117
<212> TYPE: PRT
<213> ORGANISM: Artificial Sequence
<220> FEATURE:
<223> OTHER INFORMATION: VH chain mAb A

<400> SEQUENCE: 10

Glu Val Lys Leu Val Glu Ser Gly Gly Gly Leu Val Lys Pro Gly Gly
1               5                   10                  15

Ser Leu Gln Leu Ser Cys Val Ala Ser Gly Phe Thr Phe Ser Ser Tyr
            20                  25                  30

Ala Met Ser Trp Val Arg Gln Thr Pro Glu Lys Gly Leu Glu Trp Val
        35                  40                  45

Ala Ser Ile Thr Ser Gly Gly Asn Thr Tyr Tyr Pro Asp Ser Val Lys
    50                  55                  60

Gly Arg Phe Thr Ile Ser Arg Asp Asn Ala Gly Asn Ile Leu Tyr Leu
65                  70                  75                  80

Gln Met Ser Ser Leu Arg Ser Glu Asp Thr Ala Met Phe Tyr Cys Ala
                85                  90                  95

Arg Glu Val Leu Ser Val Pro Phe Ala Tyr Trp Gly Gln Gly Thr Leu
            100                 105                 110
```

```
Val Thr Val Ser Thr
        115


<210> SEQ ID NO 11
<211> LENGTH: 123
<212> TYPE: PRT
<213> ORGANISM: Artificial Sequence
<220> FEATURE:
<223> OTHER INFORMATION: VH chain mAb B

<400> SEQUENCE: 11

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Asp Lys Arg Leu Glu Trp Val
        35                  40                  45

Ala Tyr Ile Thr Ser Gly Val Gly Asn Leu Asn Tyr Leu Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Phe Cys
                85                  90                  95

Leu Arg Pro Pro Ser Tyr Phe Gly Ser Ser Tyr Asp Ala Met Asp Tyr
            100                 105                 110

Trp Gly Arg Gly Thr Ser Val Thr Val Ser Ser
        115                 120


<210> SEQ ID NO 12
<211> LENGTH: 118
<212> TYPE: PRT
<213> ORGANISM: Artificial Sequence
<220> FEATURE:
<223> OTHER INFORMATION: VH chain mAb D

<400> SEQUENCE: 12

Gln Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Gln Leu Tyr Trp Val Lys Gln Ser His Gly Lys Ser Leu Glu Trp Ile
        35                  40                  45

Gly Tyr Ile Asp Pro Tyr Asn Gly Gly Thr Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Ser Pro Arg Trp Leu Pro Ala Gly Asp Tyr Trp Gly Gln Gly Thr
            100                 105                 110

Ser Val Thr Val Ser Ser
        115


<210> SEQ ID NO 13
<211> LENGTH: 107
<212> TYPE: PRT
<213> ORGANISM: Artificial Sequence
<220> FEATURE:
<223> OTHER INFORMATION: CL chain mAbs A,B and D
```

<400> SEQUENCE: 13

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 14
<211> LENGTH: 323
<212> TYPE: PRT
<213> ORGANISM: Artificial Sequence
<220> FEATURE:
<223> OTHER INFORMATION: CH Chain mAbs A and B

<400> SEQUENCE: 14

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
```

```
            245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly


<210> SEQ ID NO 15
<211> LENGTH: 11
<212> TYPE: PRT
<213> ORGANISM: Artificial Sequence
<220> FEATURE:
<223> OTHER INFORMATION: CDR 1 VL mAb A

<400> SEQUENCE: 15

Arg Ala Ser Gln Asp Ile Ser Asn Tyr Leu His
1               5                   10


<210> SEQ ID NO 16
<211> LENGTH: 7
<212> TYPE: PRT
<213> ORGANISM: Artificial Sequence
<220> FEATURE:
<223> OTHER INFORMATION: CDR 2 VL mAb A

<400> SEQUENCE: 16

Tyr Thr Ser Arg Leu His Ser
1               5


<210> SEQ ID NO 17
<211> LENGTH: 9
<212> TYPE: PRT
<213> ORGANISM: Artificial Sequence
<220> FEATURE:
<223> OTHER INFORMATION: CDR 3 VL mAb A

<400> SEQUENCE: 17

Gln Gln Gly Asn Ser Phe Pro Trp Thr
1               5


<210> SEQ ID NO 18
<211> LENGTH: 11
<212> TYPE: PRT
<213> ORGANISM: Artificial Sequence
<220> FEATURE:
<223> OTHER INFORMATION: CDR 1 VL mAb B

<400> SEQUENCE: 18

Arg Ala Ser Gln Ser Ile Ser Asp Asn Leu His
1               5                   10


<210> SEQ ID NO 19
<211> LENGTH: 7
<212> TYPE: PRT
<213> ORGANISM: Artificial Sequence
<220> FEATURE:
<223> OTHER INFORMATION: CDR 2 VL mAb B

<400> SEQUENCE: 19

Tyr Ser Ser Gln Ser Ile Ser
```

1 5

<210> SEQ ID NO 20
<211> LENGTH: 9
<212> TYPE: PRT
<213> ORGANISM: CDR 3 VL mAb B
<220> FEATURE:
<223> OTHER INFORMATION: Tissue plasminogen activator signal peptide

<400> SEQUENCE: 20

Gln Gln Ser Asn Ser Trp Pro Phe Thr
1 5

<210> SEQ ID NO 21
<211> LENGTH: 16
<212> TYPE: PRT
<213> ORGANISM: Artificial Sequence
<220> FEATURE:
<223> OTHER INFORMATION: CDR 1 VL mAb D

<400> SEQUENCE: 21

Arg Ser Ser Gln Ser Leu Val Asn Ser Asp Gly Asn Thr Phe Leu Gln
1 5 10 15

<210> SEQ ID NO 22
<211> LENGTH: 7
<212> TYPE: PRT
<213> ORGANISM: Artificial Sequence
<220> FEATURE:
<223> OTHER INFORMATION: CDR 2 VL mAb D

<400> SEQUENCE: 22

Lys Val Ser Asn Arg Phe Ser
1 5

<210> SEQ ID NO 23
<211> LENGTH: 9
<212> TYPE: PRT
<213> ORGANISM: Artificial Sequence
<220> FEATURE:
<223> OTHER INFORMATION: CDR 3 VL mAb D

<400> SEQUENCE: 23

Ser Gln Ser Thr His Val Pro Trp Thr
1 5

<210> SEQ ID NO 24
<211> LENGTH: 7
<212> TYPE: PRT
<213> ORGANISM: Artificial Sequence
<220> FEATURE:
<223> OTHER INFORMATION: CDR 1 VH mAb A

<400> SEQUENCE: 24

Gly Phe Thr Phe Ser Ser Tyr
1 5

<210> SEQ ID NO 25
<211> LENGTH: 5
<212> TYPE: PRT
<213> ORGANISM: Artificial Sequence
<220> FEATURE:
<223> OTHER INFORMATION: CDR 2 VH mAb A

<400> SEQUENCE: 25

Thr Ser Gly Gly Asn
1 5

<210> SEQ ID NO 26
<211> LENGTH: 9
<212> TYPE: PRT
<213> ORGANISM: Artificial Sequence
<220> FEATURE:
<223> OTHER INFORMATION: CDR 3 VH mAb A

<400> SEQUENCE: 26

Glu Val Leu Ser Val Pro Phe Ala Tyr
1               5

<210> SEQ ID NO 27
<211> LENGTH: 7
<212> TYPE: PRT
<213> ORGANISM: Artificial Sequence
<220> FEATURE:
<223> OTHER INFORMATION: CDR 1 VH mAb B

<400> SEQUENCE: 27

Gly Phe Ala Phe Ser Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: CDR 2 VH mAb B

<400> SEQUENCE: 28

Thr Ser Gly Val Gly Asn
1               5

<210> SEQ ID NO 29
<211> LENGTH: 14
<212> TYPE: PRT
<213> ORGANISM: Artificial Sequence
<220> FEATURE:
<223> OTHER INFORMATION: CDR 3 VH mAb B

<400> SEQUENCE: 29

Pro Pro Ser Tyr Phe Gly Ser Ser Tyr Asp Ala Met Asp Tyr
1               5                   10

<210> SEQ ID NO 30
<211> LENGTH: 7
<212> TYPE: PRT
<213> ORGANISM: Artificial Sequence
<220> FEATURE:
<223> OTHER INFORMATION: CDR 1 VH mAb D

<400> SEQUENCE: 30

Gly Tyr Ala Phe Thr Ser Tyr
1               5

<210> SEQ ID NO 31
<211> LENGTH: 6
<212> TYPE: PRT
<213> ORGANISM: Artificial Sequence
<220> FEATURE:
<223> OTHER INFORMATION: CDR 2 VH mAb D

<400> SEQUENCE: 31

Asp Pro Tyr Asn Gly Gly
1               5

<210> SEQ ID NO 32
<211> LENGTH: 9
<212> TYPE: PRT
<213> ORGANISM: Artificial Sequence
<220> FEATURE:
<223> OTHER INFORMATION: CDR 3 VH mAb D

<400> SEQUENCE: 32

Pro Arg Trp Leu Pro Ala Gly Asp Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: Epitope mAb D

<400> SEQUENCE: 33

Pro Ile Ala Pro Gly Gln Met
1               5

<210> SEQ ID NO 34
<211> LENGTH: 330
<212> TYPE: PRT
<213> ORGANISM: Artificial Sequence
<220> FEATURE:
<223> OTHER INFORMATION: CH Chain mAb D

<400> SEQUENCE: 34

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Thr Pro Lys Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu

```
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330


<210> SEQ ID NO 35
<211> LENGTH: 279
<212> TYPE: PRT
<213> ORGANISM: Artificial Sequence
<220> FEATURE:
<223> OTHER INFORMATION: P24 Antigen Variant 1
<220> FEATURE:
<221> NAME/KEY: SITE
<222> LOCATION: (18)..(18)
<223> OTHER INFORMATION: Xaa is any amino acid

<400> SEQUENCE: 35

Ala Leu Asp Lys Ile Glu Glu Glu Gln Asn Lys Ser Lys Lys Lys Ala
1               5                   10                  15

Gln Xaa Ala Ala Ala Ala Asp Ala Gly Asn Ser Ser Gln Val Ser Gln
            20                  25                  30

Asn Tyr Pro Ile Val Gln Asn Leu Gln Gly Gln Met Val His Gln Ala
        35                  40                  45

Ile Ser Pro Arg Thr Leu Asn Ala Trp Val Lys Val Val Glu Glu Lys
    50                  55                  60

Ala Phe Ser Pro Glu Val Ile Pro Met Phe Ser Ala Leu Ser Glu Gly
65                  70                  75                  80

Ala Thr Pro Gln Asp Leu Asn Thr Met Leu Asn Thr Val Gly Gly His
                85                  90                  95

Gln Ala Ala Met Gln Met Leu Lys Glu Thr Ile Asn Glu Glu Ala Ala
            100                 105                 110

Glu Trp Asp Arg Leu His Pro Val His Ala Gly Pro Ile Ala Pro Gly
        115                 120                 125

Gln Met Arg Glu Pro Arg Gly Ser Asp Ile Ala Gly Thr Thr Ser Thr
    130                 135                 140

Leu Gln Glu Gln Ile Gly Trp Met Thr Asn Asn Pro Pro Ile Pro Val
145                 150                 155                 160

Gly Glu Ile Tyr Lys Arg Trp Ile Ile Leu Gly Leu Asn Lys Ile Val
                165                 170                 175

Arg Met Tyr Ser Pro Thr Ser Ile Leu Asp Ile Arg Gln Gly Pro Lys
            180                 185                 190

Glu Pro Phe Arg Asp Tyr Val Asp Arg Phe Tyr Lys Thr Leu Arg Ala
        195                 200                 205

Glu Gln Ala Ser Gln Glu Val Lys Asn Trp Met Thr Glu Thr Leu Leu
    210                 215                 220

Val Gln Asn Ala Asn Pro Asp Cys Lys Thr Ile Leu Lys Ala Leu Gly
225                 230                 235                 240
```

```
Pro Ala Ala Thr Leu Glu Glu Met Met Thr Ala Cys Gln Gly Val Gly
                245                 250                 255

Gly Pro Gly His Lys Ala Arg Val Leu Ala Glu Ala Met Ser Gln Val
            260                 265                 270

Thr Asn Asn Ser Ala Thr Ile
        275
```

<210> SEQ ID NO 36
<211> LENGTH: 232
<212> TYPE: PRT
<213> ORGANISM: Artificial Sequence
<220> FEATURE:
<223> OTHER INFORMATION: P24 Antigen Variant 2

<400> SEQUENCE: 36

```
Met Pro Ile Val Gln Asn Leu Gln Gly Gln Met Val His Gln Ala Ile
1               5                   10                  15

Ser Pro Arg Thr Leu Asn Ala Trp Val Lys Val Val Glu Glu Lys Ala
            20                  25                  30

Phe Ser Pro Glu Val Ile Pro Met Phe Ser Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80

Trp Arg Asp Val His Pro Val His Ala Gly Pro Ile Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr Asn Asn Pro Pro Ile Pro Val Gly
        115                 120                 125

Glu Ile Tyr Lys Arg Trp Ile Ile Leu Gly Leu Asn Lys Ile Val Arg
    130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Asp Val Lys Asn Trp Met Thr Glu Thr Leu Leu Val
            180                 185                 190

Gln Asn Ala Asn Pro Asp Cys Lys Thr Ile Leu Lys Ala Leu Gly Pro
        195                 200                 205

Ala Ala Thr Leu Glu Glu Met Met Thr Ala Cys Gln Gly Val Gly Gly
    210                 215                 220

Pro Gly His Lys Ala Arg Val Leu
225                 230
```

<210> SEQ ID NO 37
<211> LENGTH: 705
<212> TYPE: DNA
<213> ORGANISM: Artificial Sequence
<220> FEATURE:
<223> OTHER INFORMATION: Nucleotide sequence for VL mAb A

<400> SEQUENCE: 37

```
atggagaccg acaccctgct gctctgggtg ctgctgctct gggtgcccgg ctccaccgga      60

gacatccaga tgacccagac caccagctcc ctgagcgcca gcctgggcga cagggtgacc     120

atcaactgca gggccagcca ggacatcagc aactacctgc actggtatca acagaagccc     180
```

```
gacggcacgg tgaaactgct gatctactat accagcaggc tgcacagcgg cgtgcccagc    240

cgcttctccg gtagcggcag cggcaccgac tactctctga ccattagcaa cctggagaag    300

gaggacattg ccacctactt ctgtcagcag ggcaacagct tcccctggac cttcggcgga    360

ggaaccaaag tggaaatcaa gcgggcagat gctgcaccaa ctgtatccat cttcccacca    420

tccagtgagc agttaacatc tggaggtgcc tcagtcgtgt gcttcttgaa caacttctac    480

cccaaagaca tcaatgtcaa gtggaagatt gatggcagtg aacgacaaaa tggcgtcctg    540

aacagttgga ctgatcagga cagcaaagac agcacctaca gcatgagcag caccctcacg    600

ttgaccaagg acgagtatga acgacataac agctatacct gtgaggccac tcacaagaca    660

tcaacttcac ccattgtcaa gagcttcaac aggaatgagt gttga                   705
```

```
<210> SEQ ID NO 38
<211> LENGTH: 1395
<212> TYPE: DNA
<213> ORGANISM: Artificial Sequence
<220> FEATURE:
<223> OTHER INFORMATION: Nucleotide sequence for VH mAb A

<400> SEQUENCE: 38
```

```
atggacccca agggcagcct gagctggaga atcctgctgt tcctgagcct ggccttcgag     60

ctgagctacg gcgaggtgaa gctcgtggag agcggcggtg gcctggttaa gcctggggga    120

agcctgcagc tgagctgcgt ggccagcggc ttcacgttca gcagctacgc catgagctgg    180

gtgaggcaga cccccgagaa gggcctggag tgggtggcaa gcatcaccag cgggggtaac    240

acctactacc ccgacagcgt gaagggcagg ttcaccatca gcagggacaa cgctggcaac    300

atcctgtacc tgcagatgag cagcctgagg agcgaggaca ccgccatgtt ctactgcgcc    360

agggaggtgc tgagcgtccc cttcgcctac tggggccagg gcaccctggt cacagtgagc    420

accgccaaga ccactccacc ttccgtgtac cctctggctc ctggatctgc cgcccagacc    480

aactccatgg tcaccctggg ctgcctcgtg aagggctact tccctgagcc tgtgaccgtg    540

acctggaact ccggctctct gtcctctggc gtgcacacct tccctgccgt gctgcagtcc    600

gacctgtaca ccctgtcctc cagcgtgacc gtgccttcct ctacctggcc ctccgagaca    660

gtgacctgca acgtggccca ccctgccagc tctaccaagg tggacaagaa aatcgtgccc    720

cgggactgcg gctgcaagcc ctgtatctgt accgtgcccg aggtgtcctc cgtgttcatc    780

ttcccaccca agcccaagga cgtgctgacc atcaccctga cccccaaagt gacctgtgtg    840

gtggtggaca tctccaagga cgacccogag gtgcagttca gttggttcgt ggacgacgtg    900

gaagtgcaca ccgctcagac ccagcccaga gaggaacagt tcaactccac cttcagatcc    960

gtgtccgagc tgcccatcat gcaccaggac tggctgaacg gcaaagagtt caagtgcaga   1020

gtgaactccg ccgccttccc agcccccatc gaaaagacca tcagcaagac caagggcaga   1080

cccaaggccc cccaggtgta cacaatcccg ccacccaaag aacagatggc caaggacaag   1140

gtgtccctga cctgcatgat caccgatttc ttcccagagg atattaccgt ggaatggcag   1200

tggaacggcc agcccgccga gaactacaag aacacccagc ctatcatgga caccgacggc   1260

tcctacttcg tgtactccaa gctgaacgtg cagaagtcca actgggaggc cggcaacacc   1320

ttcacctgta gcgtgctgca cgagggcctg cacaatcacc acaccgagaa gtccctgtcc   1380

cactcccctg gctag                                                    1395
```

```
<210> SEQ ID NO 39
```

<211> LENGTH: 705
<212> TYPE: DNA
<213> ORGANISM: Artificial Sequence
<220> FEATURE:
<223> OTHER INFORMATION: Nucleotide sequence for VL mAb B

<400> SEQUENCE: 39

```
atggagaccg acaccctgct gctctgggtg ctgctgctct gggtgcccgg ctccaccgga     60

gacatcgtgc tgacccagag ccctgccacc ctgagcgtga cccctggcga cagcgtgagc    120

ctgagctgca gggccagcca gagcattagc gacaacctgc actggtacag gcagaaaagc    180

cacgaaagcc ccaggcttct gatcaagtac agcagccaaa gcatctcagg catccccagc    240

aggttcagtg ggagcggcag cggcaccgac ttcaccctgt ccatcaacag cgttgagacc    300

gaggacttcg gcatgtactt ctgccagcag agcaacagct ggccgtttac cttcggctcc    360

ggcactaacc tggagctgaa gcgggcagat gctgcaccaa ctgtatccat cttcccacca    420

tccagtgagc agttaacatc tggaggtgcc tcagtcgtgt gcttcttgaa caacttctac    480

cccaaagaca tcaatgtcaa gtggaagatt gatggcagtg aacgacaaaa tggcgtcctg    540

aacagttgga ctgatcagga cagcaaagac agcacctaca gcatgagcag caccctcacg    600

ttgaccaagg acgagtatga acgacataac agctatacct gtgaggccac tcacaagaca    660

tcaacttcac ccattgtcaa gagcttcaac aggaatgagt gttga                    705
```

<210> SEQ ID NO 40
<211> LENGTH: 1413
<212> TYPE: DNA
<213> ORGANISM: Artificial Sequence
<220> FEATURE:
<223> OTHER INFORMATION: Nucleotide sequence for VH mAb B

<400> SEQUENCE: 40

```
atggacccca agggcagcct gagctggaga atcctgctgt tcctgagcct ggccttcgag     60

ctgagctacg gcgaggtgca gctggtggag agcgggggtg gacttgtgaa gcccggtggc    120

tcactgaagc tgagctgcgc ggcaagcggc ttcgccttca gcagctacga catgagctgg    180

gtgaggcaga cccccgacaa gaggctggag tgggtggcct acatcaccag tggcgtgggc    240

aacctgaact acctggacac cgtgaagggc aggttcacca tcagcaggga caacgccaag    300

aacaccctgt acctgcagat gagcagcttg aggagcgaag acaccgccat gtacttctgc    360

ctgagaccgc ccagctactt cggctctagc tatgatgcca tggactactg gggcaggggt    420

actagcgtga ccgtgagctc tgccaagacc actccacctt ccgtgtaccc tctggctcct    480

ggatctgccg cccagaccaa ctccatggtc accctgggct gcctcgtgaa gggctacttc    540

cctgagcctg tgaccgtgac ctggaactcc ggctctctgt cctctggcgt gcacaccttc    600

cctgccgtgc tgcagtccga cctgtacacc ctgtcctcca gcgtgaccgt gccttcctct    660

acctggccct ccgagacagt gacctgcaac gtggcccacc ctgccagctc taccaaggtg    720

gacaagaaaa tcgtgccccg ggactgcggc tgcaagccct gtatctgtac cgtgcccgag    780

gtgtcctccg tgttcatctt cccacccaag cccaaggacg tgctgaccat caccctgacc    840

cccaaagtga cctgtgtggt ggtggacatc tccaaggacg accccgaggt gcagttcagt    900

tggttcgtgg acgacgtgga agtgcacacc gctcagaccc agcccagaga ggaacagttc    960

aactccacct tcagatccgt gtccgagctg cccatcatgc accaggactg gctgaacggc   1020

aaagagttca agtgcagagt gaactccgcc gccttcccag cccccatcga aaagaccatc   1080

agcaagacca agggcagacc caaggccccc caggtgtaca caatcccgcc acccaaagaa   1140
```

cagatggcca aggacaaggt gtccctgacc tgcatgatca ccgatttctt cccagaggat 1200
attaccgtgg aatggcagtg gaacggccag cccgccgaga actacaagaa cacccagcct 1260
atcatggaca ccgacggctc ctacttcgtg tactccaagc tgaacgtgca gaagtccaac 1320
tgggaggccg gcaacacctt cacctgtagc gtgctgcacg agggcctgca caatcaccac 1380
accgagaagt ccctgtccca ctcccctggc tag 1413

<210> SEQ ID NO 41
<211> LENGTH: 720
<212> TYPE: DNA
<213> ORGANISM: Artificial Sequence
<220> FEATURE:
<223> OTHER INFORMATION: Nucleotide sequence for VL mAb D

<400> SEQUENCE: 41
atggagaccg acaccctgct gctctgggtg ctgctgctct gggtgcccgg ctccaccgga 60
gacgtggtga tgacccagac acccctgagt ctgcccgtga gcttgggcga ccaggccagc 120
atcagctgta ggagctcaca gagcctggtg aacagcgacg gcaacacctt cctgcagtgg 180
ctcctgcaaa aacccggcca aagcccgaag ctgcttatat acaaggtgag caataggttc 240
agtggtgtgc ccgaccgctt cagcggcagc ggtagcggca ccgacttcac cctgaggatc 300
agcagggtgg aggccgagga cctgggcgtg tacttctgca gccagagcac ccacgtgccc 360
tggaccttcg gcggaggaac caaactggaa atcaagcggg cagatgctgc accaactgta 420
tccatcttcc caccatccag tgagcagtta acatctggag gtgcctcagt cgtgtgcttc 480
ttgaacaact tctaccccaa agacatcaat gtcaagtgga agattgatgg cagtgaacga 540
caaaatggcg tcctgaacag ttggactgat caggacagca aagacagcac ctacagcatg 600
agcagcaccc tcacgttgac caaggacgag tatgaacgac ataacagcta tacctgtgag 660
gccactcaca agacatcaac ttcacccatt gtcaagagct tcaacaggaa tgagtgttga 720

<210> SEQ ID NO 42
<211> LENGTH: 1404
<212> TYPE: DNA
<213> ORGANISM: Artificial Sequence
<220> FEATURE:
<223> OTHER INFORMATION: Nucleotide sequence for VH mAb D

<400> SEQUENCE: 42
atggagaccg acaccctgct gctctgggtg ctgctgctct gggtgcccgg ctccaccgga 60
cagatccagc tgcaacaaag cggccctgag ctggtgaagc ccggtgctag cgtgaaggtg 120
agctgtaagg caagcggcta cgccttcaca agttaccagc tgtactgggt aaagcaaagc 180
cacggcaaga gcctggagtg gatcggctat atcgacccct acaacggcgg caccggctac 240
aaccagaagt tcaagggtaa ggccaccttg accgtggaca agagcagcag caccgcctac 300
atgcatctga acagcctgac cagcgaggac agcgccgtgt actactgcgc cagccccagg 360
tggcttcccg ctggcgacta ctggggccag ggcaccagcg tgactgtgag ctctgctaaa 420
acaacagccc catcggtcta tccactggcc cctgtgtgtg gagatacaac tggctcctcg 480
gtgactctag gatgcctggt caagggttat ttccctgagc cagtgacctt gacctggaac 540
tctggttccc tgtccagtgg tgtgcacacc ttcccagctg tcctgcagtc tgacctctac 600
accctcagct caagcgtgac tgtaaccagc tcgacctggc ccagccagtc catcacctgc 660
aatgtggccc acccggcaag cagcaccaag gtggacaaga aaattgagcc cagagggccc 720

-continued

| | |
|---|---|
| acaatcaagc cctgtcctcc atgcaaatgc ccagcaccta acctcttggg tggaccatcc | 780 |
| gtcttcatct tccctccaaa gatcaaggat gtactcatga tctccctgag ccccatagtc | 840 |
| acatgtgtag tcgttgatgt gagcgaggat gacccagatg tccagatcag ctggtttgtg | 900 |
| aacaacgtgg aagtgcacac tgctcagaca cagacgcata gagaggatta caacagtact | 960 |
| ctccgggttg tcagtgccct ccccatccag caccaggact ggatgagtgg caaggagttc | 1020 |
| aaatgcaagg tcaacaacaa agacctccca gcgcccatcg agagaaccat ctcaaaaccc | 1080 |
| aaagggtcag taagagctcc acaggtatat gtcttgcctc caccagaaga ggagatgact | 1140 |
| aagaaacagg tcactctgac ctgcatggtc acagacttca tgcctgaaga catttacgtg | 1200 |
| gagtggacca acaacgggaa aacagagcta aactacaaga acactgaacc agtcctggac | 1260 |
| tctgatggtt cttacttcat gtacagcaag ctgagagtgg agaagaagaa ctgggtggag | 1320 |
| agaaatagct actcctgttc agtggtccac gagggtctgc acaatcacca cacgactaag | 1380 |
| agcttctccc ggactccggg ttag | 1404 |